US008440412B2

(12) United States Patent
Nakanishi et al.

(10) Patent No.: US 8,440,412 B2
(45) Date of Patent: May 14, 2013

(54) COMPOSITIONS, METHODS AND ANIMAL MODELS FOR SCREENING THERAPEUTICS FOR TH2-TYPE DISEASE

(75) Inventors: Kenji Nakanishi, Hyogo (JP); Tomohiro Yoshimoto, Hyogo (JP)

(73) Assignee: Hyogo College of Medicine, Nishinomiya-shi, Hyogo (JP)

( * ) Notice: Subject to any disclaimer, the term of this patent is extended or adjusted under 35 U.S.C. 154(b) by 0 days.

(21) Appl. No.: 13/125,090

(22) PCT Filed: Oct. 26, 2009

(86) PCT No.: PCT/JP2009/005625
§ 371 (c)(1),
(2), (4) Date: Jun. 10, 2011

(87) PCT Pub. No.: WO2010/050167
PCT Pub. Date: May 6, 2010

(65) Prior Publication Data
US 2011/0252487 A1    Oct. 13, 2011

(30) Foreign Application Priority Data

Oct. 31, 2008  (JP) ................................. 2008-281930
Oct. 26, 2009  (WO) .................. PCT/JP2009/005625

(51) Int. Cl.
*G01N 33/53* (2006.01)
(52) U.S. Cl.
USPC ......... 435/7.1; 435/325; 424/184.1; 424/805; 424/810; 800/3
(58) Field of Classification Search ........................ None
See application file for complete search history.

(56) References Cited

FOREIGN PATENT DOCUMENTS

EP            619323 A1 * 10/1994
JP      2008-164523 A    7/2008

OTHER PUBLICATIONS

Bout et al., Immunology. Jul. 1997;33(1):17-22.*
Eckl-Dorna et al., Allergy. May 2012;67(5):601-8. doi: 10.1111/j.1398-9995.2012.02792.x. Epub Feb. 16, 2012. (abstract only).*
Kitzmüller et al., Allergy. May 2012;67(5):593-600. doi: 10.1111/j.1398-9995.2011.02764.x. Epub Dec. 20, 2011. (abstract only).*
Wicklein et al., Clin Exp Allergy. Apr. 2006;36(4):531-42.*
Yoshimoto et al., Nat Immunol. Jul. 2009;10(7):706-12. Epub May 24, 2009.*
Lundberg et al., Clin Immunol. Sep. 2008;128(3):358-65. Epub Jun. 26, 2008.*
Weyer et al., Agents Actions. Apr. 1987;20(3-4):210-2.*
Nyakeriga et al., Acta Trop. Apr. 2003;86(1):55-62.*
Zuberi, Riaz, I., et al., "Role for IgE in Airway Secretions: IgE Immune Complexes Are More Potent Inducers Than Antigen Alone of Airway Inflammation in a Murine Model," Journal of Immunology, vol. 164, No. 5, Mar. 1, 2000, pp. 2667-2673.

Pirron, Ulrich, et al., "IgE-dependent antigen focusing by human B lymphocytes is mediated by the low-affinity receptor for IgE*," European Journal of Immunology, vol. 20, No. 7, Jul. 1990, pp. 1547-1551.
Wedemeyer, Jochen, et al., "Roles of mast cells and basophils in innate and acquired immunity," Current Opinion in Immunology, Elsevier, Oxford, GB, vol. 12, No. 6, Dec. 1, 2000, pp. 624-631.
Schramm, Gabriele, et al., "Cutting Edge: IPSE/alpha-1, a Glycoprotein from Schistosoma mansoni Eggs, Induces IgE-Dependent, Antigen-Independent IL-4 Production by Murine Basophils in Vivo," Journal of Immunology, vol. 178, No. 10, May 15, 2007, pp. 6023-6027.
Poncet, Pascal, et al., "MHC class II-dependent activation of CD4+ T cell hybridomas by human mast cells through superantigen presentation," Journal of Leukocyte Biology, vol. 66, No. 1, Jul. 1999, pp. 105-112.
Letourneur, Francois and Klausner, Richard D., "T-cell and basophil activation through the cytoplasmic tail of T-cell-receptor & family proteins," Proceedings of the National Academy of Sciences, USA, vol. 88, Oct. 1, 1991, pp. 8905-8909.
Sokol, Caroline L., et al., "Basophils function as antigen-presenting cells for an allergen-induced T helper type 2 response," Nature Immunology, vol. 10, No. 7, Jul. 2009, pp. 713-720.
International Search Report dated Nov. 24, 2009 and English Translation; International Patent Application No. PCT/JP2009/005625.
Galli, Stephen J. MD, "Mast Cells and Basophils," Current Opinion in Hematology, 7:32-39 (2000).
Galli, Stephen J., et al., "Mast Cells as 'Tunable' Effector and Immunoregulatory Cells: Recent Advances," Annu. Rev. Immunol., 23:749-786 (2005).
Kawakami, et al., "Regulation of Mast-Cell and Basophil Function and Survival by IgE," Nature Reviews / Immunology, 2: 773-786 (Oct. 2002).
Mukai, Kaori, et al., "Basophils Play a Critical Role in the Development of IgE-Mediated Chronic Allergic Inflammation, Independently of T Cells and Mast Cells," Immunity, vol. 23, 191-202 (Aug. 2005).
Min, Booki, et al., "Basophils Produce IL-4 and Accumulate in Tissues after Infection with a Th2-inducing Parasite," The Journal of Experimental Medicine, 200, 4:507-517 (Aug. 16, 2004).
Tsujimura, Yusuke, et al., "21st Century Renaissance of Basophils—Unique roles of basophils in the living body being revealed one after another-", The Japanese Journal of Clinical Hematology, vol. 49, No. 7, pp. 489-497 (Jul. 30, 2008); (Partial English Translation).
Sokol, Caroline L., et al., "A mechanism for the initiation of allergen-induced T helper type 2 responses," Nature Immunology, vol. 9, No. 3, pp. 310-318 (Mar. 2008).
Kojima, Toshiyuki, et al., "Mast Cells and Basophils are Selectively Activated in Vitro and In Vivo Through CD200R3 in an IgE-Independent Manner," The Journal of Immunology, vol. 179:7093-7100 (2007).
Obata, Kazushige, et al., "Basophils are essential initiators of a novel (Continued)

*Primary Examiner* — Michael Szperka
(74) *Attorney, Agent, or Firm* — Casimir Jones SC

(57) ABSTRACT

The present invention provides a complex of an antigen and IgE binding to the antigen, a composition including an antigen and IgE binding to the antigen, and a method of using the complex or the composition to screen candidate therapeutics for TH-2 type diseases, for example in animal models.

4 Claims, 13 Drawing Sheets

OTHER PUBLICATIONS type of chronic allergic inflammation," Blood, vol. 110, No. 3:913-920 (Aug. 1, 2007).

Nakanishi, Kenji, et al., "Basophils induce and augment Th2 response," Proceedings of the Japanese Society for Immunology, vol. 38: P2, S2-1 (2008).

Yoshimoto, Tomohiro, et al., "Basophils contribute to TH2-IgE responses in vivo via IL-4 production and presentation of peptide-MHC class II complexes to CD4+ T Cells," Nature Immunology, vol. 10, No. 7:706-712 (Jul. 2009).

* cited by examiner

FIG. 1 (a)
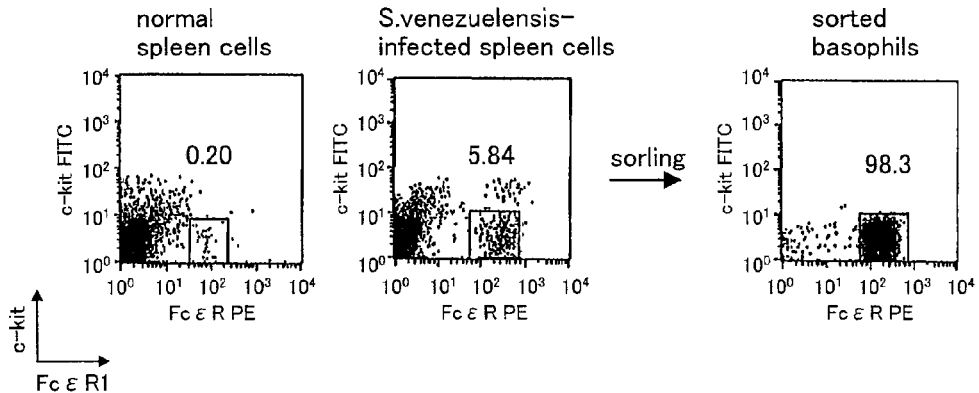
FIG. 1 (b)
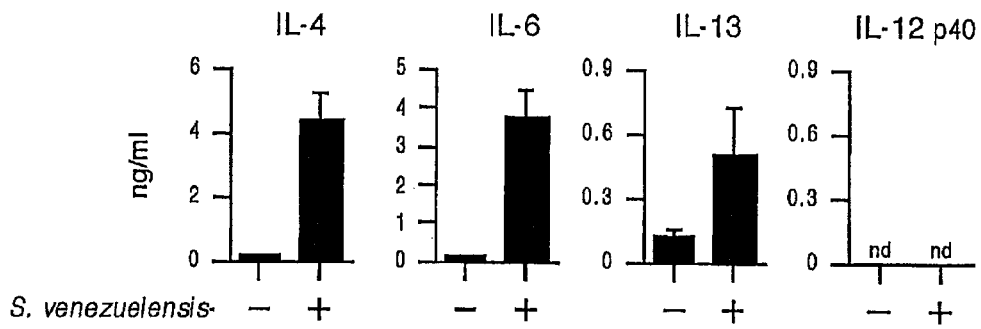
FIG. 1 (c)
FIG. 1 (d)
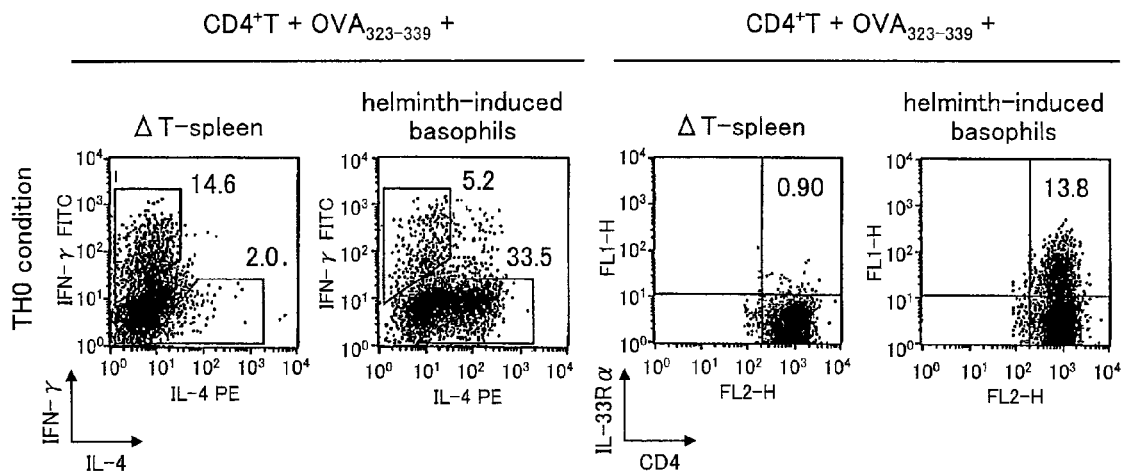

COMPOSITIONS, METHODS AND ANIMAL MODELS FOR SCREENING THERAPEUTICS FOR TH2-TYPE DISEASE

CROSS REFERENCE TO RELATED APPLICATIONS

The present application is a Section 371 U.S. national stage entry of pending International Patent Application No. PCT/JP2009/005625, International Filing Date Oct. 26, 2009, which published on May 6, 2010 as Publication No. WO 2010/050167, which claims the benefit of Japanese Patent Application No. 281930/2008, filed Oct. 31, 2008, the contents of which are incorporated by reference in their entireties.

TECHNICAL FIELD

The present invention relates to a composition for inducing Th2 cells and use of such a composition, and particularly relates to a composition for producing early IL-4 that causes Th2 immune response and use of such a composition. Moreover, the present invention relates to a composition for treating Th2-type disease and use of such a composition, and particularly relates to a composition for blocking production of the early IL-4 that causes the Th2 immune response and use of such a composition.

2. Background Art

Macrophage and dendritic cells (DCs) act against entry of invading bacteria as follows. Upon entry of invading bacteria, the DCs recognize the bacteria through Toll-like receptors (TLR) and mature to (i) express co-stimulatory molecules and to (ii) produce IL-12 and IL-18 which induce Th1 immune response. Naive T cells develop into Th1 cells as a result of the naive T cells binding with the macrophage or DCs by being mediated by the co-stimulatory molecules, together with an action of IL-12. IFN-γ secreted from the Th1 cells activates the macrophage, by which causes activation of effects such as phagocytosis and bactericidal actions.

The naive T cells develop into Th1 cells caused by IL-12, and develop into Th2 cells caused by IL-4. Together with Th1 cells, Th2 cells are important cells in the adaptive immune system. However, the role of innate immune cells in development of the Th2 immune response is poorly understood.

Basophils and mast cells are important effector cells in IgE-mediated allergic inflammation (see Non Patent Literatures 1 to 4). Moreover, infection with parasites strongly induces Th2 cells and proliferation of basophils in the spleens and livers of host mice (see Non Patent Literature 5). This suggests a contribution of basophils to the induction and/or augmentation of Th2 responses.

CITATION LIST

Non Patent Literatures
Non Patent Literature 1
Galli, S. J. Curr Opin Hematol 7: 32-9 (2000)
Non Patent Literature 2
Galli, S. J. et al. Annu Rev Immunol 23: 749-86 (2005)
Non Patent Literature 3
Kawakami, T. & Galli, S. J. Nat Rev Immunol 2: 773-86 (2002)
Non Patent Literature 4
Mukai, K. et al. Immunity 23: 191-202 (2005) Non Patent Literature 5
Min, B. et al. J Exp Med 200: 507-17 (2004)

SUMMARY OF INVENTION

Technical Problem

However, the nature of cells that produce early IL-4, which is required for the development of naive CD4$^+$ T cells into Th2 cells, remains unknown. Moreover, initial stimulation for producing early IL-4 is not understood as to what substance causes the initial stimulation. Furthermore, a mechanism of how innate immune cells induce the development into Th2 cells has also not been understood.

The present invention is accomplished in view of these problems, and an object thereof is to provide a technique for treating and preventing Th2-type diseases, by clarifying a working mechanism of a Th2 immune response, particularly by clarifying a mechanism of how early IL-4 is produced.

Solution to Problem

The inventors of the present invention found that basophils internalize and process an antigen, present the processed antigen on a surface thereof and produce IL-4, and further that naive T cells recognize antigen peptide/MHC class II molecule complex presented on the surface of the basophils in the presence of IL-4, whereby causing the naive T cells to be induced to develop into Th2 cells. The inventors then observed that the induction of the naive T cells to develop into the Th2 cells causes activation of B cells which are stimulated by the induction, and as a result IgE corresponding to an antigen is produced. The present invention was accomplished based on these findings. Namely, a composition according to the present invention includes basophils, for inducing the development of naive T cells into Th2 cells. It is further preferable that the composition according to the present invention include an antigen, and is more preferable that the composition further include IgE binding to the antigen.

The composition according to the present invention is usable in a method of inducing the development of naive T cells into Th2 cells. Namely, a method of inducing to develop Th2 cells according to the present invention includes the steps of: (a) producing a complex of an antigen and IgE binding to the antigen; (b) culturing basophils in the presence of the complex; and (c) culturing naive T cells with the basophils cultured in the step (b).

A composition according to the present invention includes basophils, for producing IL-4. It is preferable that the composition according to the present invention further include an antigen, and is more preferable to further include IgE binding to the antigen.

The composition according to the present invention is usable in a method of producing IL-4. Namely, a method of producing IL-4 according to the present invention includes the steps of: (a) producing a complex of an antigen and IgE binding to the antigen; and (b) culturing basophils in the presence of the complex. With use of the present method, it is possible to produce IL-4, particularly early IL-4 (primary IL-4). Moreover, the method of producing IL-4 according to the present invention includes the steps of: (a) producing a complex of an antigen and IgE binding to the antigen; (b) culturing basophils in the presence of the complex; and (c) culturing naive T cells with the basophils cultured in the step (b). With use of the present method, it is possible to produce IL-4, particularly secondary IL-4.

A composition according to the present invention includes basophils, for producing IgE. It is preferable that the composition according to the present invention further include an antigen, and is more preferable that the composition further include IgE binding to the antigen.

The composition according to the present invention is usable in a method of producing IgE. Namely, a method of producing IgE according to the present invention includes the steps of: (a) producing a complex of an antigen and IgE binding with the antigen; (b) culturing basophils in the presence of the complex; (c) culturing naive T cells with the basophils cultured in the step (b); and (d) culturing B cells with Th2 cells induced in the step (c), in the presence of the antigen and antigen-presenting cells. With use of the present method, it is possible to produce IgE, particularly early IgE (primary IgE). Moreover, the method of producing IgE according to the present invention includes the steps of: (a) producing a complex of an antigen and IgE binding to the antigen; (b) culturing basophils in the presence of the complex; (c) culturing naive T cells with the basophils cultured in the step (b); (d) culturing B cells with Th2 cells induced in the step (c), in the presence of the antigen and antigen-presenting cells, to produce IgE; and (e) culturing the antigen, the Th2 cells and the B cells, in the presence of IgE produced in the step (d). With use of the present method, it is possible to produce IgE, particularly secondary IgE.

A composition according to the present invention includes basophils, for screening a therapeutic agent of a Th2-type disease. It is preferable that the composition according to the present invention further include an antigen, and is more preferable that the composition further include IgE binding to the antigen. The Th2-type disease is preferably selected from the group consisting of: hay fever, bronchial asthma, atopic dermatitis, allergic enteritis, allergic conjunctivitis, and allergic rhinitis.

The composition according to the present invention is usable in a method of screening a therapeutic agent of a Th2-type disease. Namely, a screening method according to the present invention includes the steps of: (a) producing a complex of an antigen and IgE binding to the antigen; and (b) culturing basophils in the presence of the complex. It is preferable that in the screening method according to the present invention, the step (b) is carried out in the presence or absence of a candidate substrate, and that the screening method further includes the step of: (f) measuring an amount of MHC class II molecules or CD80 molecules presented on a cell surface of the basophils having been subjected to the step (b).

Moreover, the screening method according to the present invention may further include the steps of: (a) producing a complex of an antigen and IgE binding the antigen; (c) culturing naive T cells with the basophils cultured in the step (b), the step (b) or the step (c) being carried out in the presence or absence of a candidate substance; and (g) measuring an amount of Th2 cells induced in the step (c).

Furthermore, the screening method according to the present invention may further include the steps of: (a) producing a complex of an antigen and IgE binding to the antigen; (d) culturing B cells with Th2 cells induced in the step (c), in the presence of the antigen and antigen-presenting cells, to produce IgE, at least one of the steps (b) to (d) being carried out in the presence or absence of a candidate substance; and (h) measuring an amount of IgE produced in the step (d).

Furthermore, the screening method according to the present invention may further include the steps of: (a) producing a complex of an antigen and IgE binding to the antigen; (e) culturing the antigen, the Th2 cells and the B cells in the presence of IgE produced in the step (d), at least one of the steps (b) to (e) being carried out in the presence or absence of a candidate substance; and (i) measuring an amount of IgE produced in the step (e).

A method of preparing a model animal according to the present invention, to prepare a Th2-type disease model animal, includes the steps of: producing a complex of an antigen and IgE binding to the antigen; culturing basophils in the presence of the complex; and administering to an animal the basophils having been cultured in the presence of the complex. The Th2-type disease is preferably selected from the group consisting of: hay fever, bronchial asthma, atopic dermatitis, allergic enteritis, allergic conjunctivitis, and allergic rhinitis. A model animal prepared by the preparation method according to the present invention may be a model animal of bronchial asthma, and in this case, it is preferable that the antigen be administered by transnasal administration after intravenously administering the basophils which have been cultured in the presence of the complex.

The model animal prepared by such a preparation method can be used for screening a therapeutic agent of a Th2-type disease. Namely, a screening method according to the present invention for screening a therapeutic agent of a Th2-type disease, includes the steps of: administering to an animal the basophils cultured in the step (b), to prepare a model animal; administering a candidate substance to the model animal; and measuring whether or not improvement is attained of the Th2-type disease, in the model animal to which the candidate substance is administered.

A composition according to the present invention, for treatment of a Th2-type disease, includes: a substance causing depletion of basophils; or a substance inhibiting a function of FcεR1. It is preferable that the composition according to the present invention includes an antibody of FcεR1.

It is preferable that a treatment method according to the present invention, for treating the Th2-type disease, include the step of: depleting basophils from a subject; or administering to a subject a substance inhibiting a function of FcεR1. It is preferable that the method according to the present invention include the step of: administering to the subject an antibody of FcεR1.

Moreover, the inventors of the present invention found that it is preferable that basophils pulsed with an antigen-IgE complex be used, and further found that an antigen-IgE complex transferred into normal mice induces a Th2 response which is caused by endogenous basophils. Namely, a feature of the complex according to the present invention is that it is made up of an antigen and IgE binding to the antigen. With use of the present invention, it is possible to produce IL-4 with use of basophils existing in peripheral blood, spleen, bone marrow and the like. Such basophils can induce the Th2 response in the spleen or the like. Moreover, the composition according to the present invention includes an antigen and IgE binding to the antigen. With use of such a composition, it is possible to produce the complex according to the present invention. This allows for inducing the Th2 response. Furthermore, a kit according to the present invention includes: an antigen; IgE binding to the antigen; and basophils. With use of such a kit, it is possible to produce the complex according to the present invention. This allows for inducing the Th2 response.

The composition according to the present invention is usable in a technique for inducing naive T cells into Th2 cells. Namely, a composition according to the present invention, for inducing the naive T cells into the Th2 cells, includes: an antigen; and IgE binding to the antigen. Moreover, a kit according to the present invention, for inducing the naive T cells into the Th2 cells, includes: an antigen; IgE binding to the antigen; and basophils.

The composition according to the present invention is usable in a technique for producing IL-4. Namely, a composition according to the present invention, for producing IL-4, includes: an antigen; and IgE binding to the antigen. Moreover, a kit according to the present invention, for producing secondary IL-4, includes: an antigen; IgE binding to the antigen; and basophils.

The composition according to the present invention is usable in a technique for producing IgE. Namely, a composition according to the present invention, for producing IgE, includes: an antigen; and IgE binding to the antigen. Moreover, a kit according to the present invention, for producing IgE, includes: an antigen; IgE binding to the antigen; and basophils.

The composition according to the present invention is usable in a technique for screening a therapeutic agent of a Th2-type disease. Namely, a composition according to the present invention, for screening a therapeutic agent of a Th2-type disease, includes: an antigen; and IgE binding to the antigen. Moreover, a kit according to the present invention, for screening a therapeutic agent of a Th2-type disease, includes: an antigen; IgE binding to the antigen; and basophils.

The composition according to the present invention is usable in a technique for preparing a model animal of the Th2-type disease. Namely, a composition according to the present invention, for preparing a Th2-type disease model animal, includes: an antigen; and IgE binding to the antigen. Moreover, a kit according to the present invention, for preparing a Th2-type disease model animal, includes: an antigen; IgE binding to the antigen; and basophils.

Advantageous Effects of Invention

According to the present invention, it is possible to clarify a working mechanism of a Th2-type immune response, particularly a production mechanism of early IL-4. Moreover, use of the present invention allows for inducing Th2 cells, producing IL-4, producing IgE, and screening a Th2 disease therapeutic agent. Furthermore, with use of the present invention, it is possible to prepare a Th2-type disease model animal.

BRIEF DESCRIPTION OF DRAWINGS

FIG. 1(a) is a view showing a result of analysis by flow cytometry for expression of FcεR1 and c-kit in splenic non-B, non-T cells from normal mice or parasite-infected mice, and a result of sorting of FcεR1$^+$/c-kit$^-$ cells (basophils).

FIG. 1(b) is a view showing cytokines contents in a supernatant of cultured sorted basophils.

FIG. 1(c) is a view showing a result of an analysis by FACS for cytosolic IL-4 and IFN-γ in CD4$^+$ T cells produced by stimulating naive T cells with OVA$_{323-339}$ in the presence of T cell-depleted mice splenocytes (ΔT-spleen) or basophils from parasite-infected mice.

FIG. 1(d) is a view showing expression of IL-33Rα chain on CD4$^+$ T cells produced by stimulating naive T cells with OVA$_{323-339}$ in the presence of T cell-depleted mice splenocytes (ΔT-spleen) or basophils from parasite-infected mice.

FIG. 5 shows results of various cytokines productions tested in the collected supernatants.

FIG. 7 is a view showing a measurement result of DNA synthesis during the final 16 hours.

DESCRIPTION OF EMBODIMENTS

Figure 2:
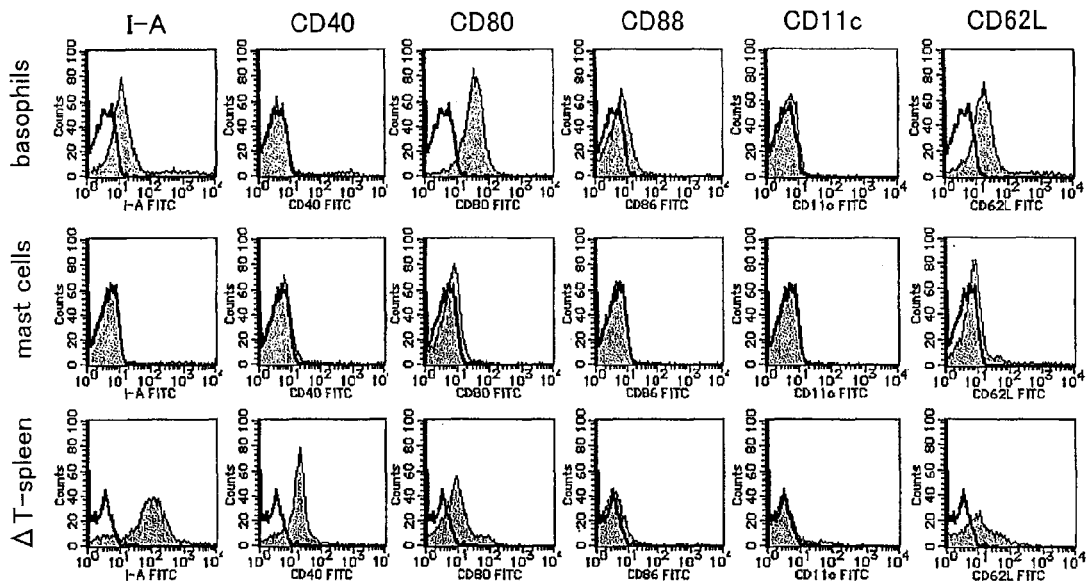
FIG. 2(a) is a view showing a result of staining, with various surface markers, bone marrow-derived and FACS sorted basophils and mast cells, and T cell-depleted splenocytes (ΔT-spleen).
FIG. 2(b) is a view showing a result of an analysis by flow cytometry of bone marrow-derived and FACS sorted basophils and mast cells, for expression of MHC class II (I-A) and FcεR1.
FIG. 2(c) is a view showing a result of an analysis by flow cytometry of CD34$^+$ cord blood cells cultured in the presence of human IL-3, for the expression of c-kit and CD203c (left) and HLA-DR among CD203c$^+$c-kit$^-$ cells (right).
Figure 2:
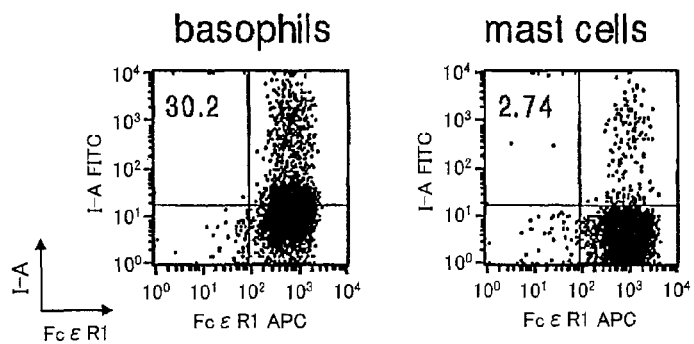
Figure 2:
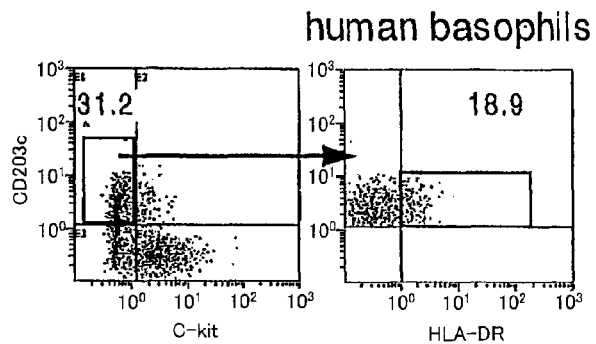

1: Basophils and Use Thereof.

It is well known that basophils and mast cells are effector cells in allergic inflammation. The inventors of the present invention found that basophils express major histocompatibility antigen class II molecules and CD80 molecules, and further found that basophils (i) internalize antigens therein, (ii) express an antigen-derived peptide fragment on a cell surface in such a manner that the antigen-derived peptide fragment is bound to a class II molecule, and (iii) produce IL-4. Furthermore, the inventors found that in normal mice, transferring of such basophils therein causes development of antigen-specific Th2 cells, intravenous administration of an OVA solution causes induction of OVA-specific IgE production, and transnasal administration of the OVA solution causes induction of bronchial asthma. As such, the present invention was accomplished based on such a new finding that cannot be easily perceived by a person skilled in the art.

A composition according to the present invention includes basophils. As described above, the inventors of the present invention found that basophils internalize and process an antigen, presents the processed antigen on the surface of the basophils, and produces IL-4. Further, it was found that naive T cells, which recognize an antigen peptide/MHC class II molecules complex presented on the surface of basophils in the presence of IL-4, develop into Th2 cells. The inventors confirmed that once Th2 cell development is induced, B cells are activated, thereby causing production of IgE of the antigen. The present invention is accomplished based on these findings. Namely, the composition according to the present invention is suitably used for inducing naive T cells to develop into Th2 cells, producing IL-4, producing IgE, and the like.

In order to internalize and process an antigen and present on the surface the processed antigen, the composition according to the present invention can be said as sufficient as long as it includes basophils. However, the composition may further include a target antigen, and is more preferable that IgE binding to the antigen is included therein, to allow for acceleration of the internalization of the target antigen. Furthermore, in order to accelerate the forming of an antigen-IgE complex to be caused to be internalized by the basophils, the antigen may be connected to hapten. In this case, IgE may be anti-hapten IgE, and in a case where it is used in the present specification, anti-hapten IgE is also included within the scope of IgE binding to the antigen.

Although preferable basophils used in the present invention can be prepared from various tissues, it is preferable to use basophils derived from tissues such as spleen, bone marrow, and like tissues. Since the percentage of basophils existing in a living body is extremely small, it is more preferable to culture and proliferate basophils obtained from the tissues, in vitro. Preferable antigens used for the present invention is not particularly limited as long as it is a protein (including peptide) that can serve as an antigen (i.e., immunogen) related to various diseases. A person skilled in the art would sufficiently know the antigens which cause Th2-type diseases; hence, the preferable antigen used in the present invention can be easily obtained based on known techniques. Moreover, a person skilled in the art who has obtained a target antigen (immunogen) can easily obtain a preferable IgE for use in the present invention, based on known techniques. In the present specification, "Th2-type disease" denotes an allergic disease caused by induction to develop into Th2 cells, and can be used exchangeably with the expression "Th2-type allergic disease". Examples of the Th2-type disease encompass: hay fever, bronchial asthma, atopic dermatitis, allergic enteritis, allergic conjunctivitis, and allergic rhinitis; however, it is not limited to these diseases.

The "composition" is a mode in which various components are included in one substance, and the "kit" is a mode in which at least one of the various components is included in a separate substance. However, in the present specification, the kit also serves to denote one mode of the composition. The wording "kit" denotes a package including a container (e.g., bottle, plate, tube, dish, etc.) that contains specific material. The kit preferably includes instructions on how to use each of the material. The wording "include" in the present specification when describing the kit denotes a state in which (i) a component is contained inside any one of individual containers that make up the kit, (ii) a plurality of components may be included in a single container and be mixed together, or (iii) a plurality of components may be included in separate containers. The "instructions" may be written or printed on paper or other mediums, or may be recorded on an electronic medium such as a magnetic tape, a computer-readable disk or tape, CD-ROM or like medium. The kit according to the present invention may also include a container containing a diluent, a solvent, a washing solution or other reagents. Furthermore, the kit according to the present invention may also include necessary equipment required for applying the present invention.

Namely, in one embodiment, the composition according to the present invention is a kit including basophils. It is further preferable that the kit according to the present embodiment include an antigen, and is more preferable that the kit include IgE binding to the antigen.

As described above, the composition according to the present invention is usable in a method of inducing naive T cells into Th2 cells. Namely, a method according to the present invention for inducing to develop Th2 cells includes the step of: (a) producing a complex of an antigen and IgE binding to the antigen; (b) culturing basophils in the presence of the complex; and (c) culturing naive T cells with the basophils cultured in the step (b).

Moreover, the composition according to the present invention is usable in a method of producing IL-4. Namely, a method of producing IL-4 according to the present invention includes the steps of: (a) producing a complex of an antigen and IgE binding to the antigen; and (b) culturing basophils in the presence of the complex. With use of the present method, it is possible to produce IL-4, particularly early IL-4 (primary IL-4). Moreover, the method of producing IL-4 according to the present invention includes the steps of: (a) producing a complex of an antigen and IgE binding to the antigen; (b) culturing basophils in the presence of the complex; and (c) culturing naive T cells with the basophils cultured in the step (b). With use of the present method, it is possible to produce IL-4, particularly secondary IL-4 (secondary IL-4).

Furthermore, the composition according to the present invention is usable in a method of producing IgE. Namely, a method of producing IgE according to the present invention includes the steps of: (a) producing a complex of an antigen and IgE binding to the antigen; (b) culturing basophils in the presence of the complex; (c) culturing naive T cells with the basophils cultured in the step (b); and culturing B cells with Th2 cells induced in the step (c), in the presence of the antigen and professional antigen-presenting cells. With use of the present method, it is possible to produce IgE, particularly early IgE (primary IgE). Moreover, a method of producing IgE according to the present invention includes the steps of: (a) producing a complex of an antigen and IgE binding with the antigen; (b) culturing basophils in the presence of the complex; (c) culturing naive T cells with the basophils cultured in the step (b); (d) culturing B cells with Th2 cells induced in the step (c), in the presence of the antigen and the professional antigen-presenting cells, to produce IgE; and (e) culturing the antigen, the Th2 cells and the B cells in the presence of the IgE produced in the step (d). With use of the present method, it is possible to produce IgE, particularly secondary IgE.

The cells cultured in the present invention are basophils, naive T cells, Th2 cells, and B cells, and culturing procedures (culturing conditions) of these cells are well known in the technical field. Hence, a person skilled in the art would be capable of appropriately designing a known culturing procedure, in carrying out the present invention.

The composition according to the present invention is suitably usable for inducing naive T cells to develop into Th2 cells, producing IL-4, producing IgE, and the like. Hence, by utilizing as an index whether the induction of the naive T cells into the Th2 cells, the production of IL-4, or the production of IgE with use of the composition according to the present invention are suppressed or inhibited, it is possible to screen therapeutic agents of Th2-type diseases. Moreover, with use of the composition according to the present invention, it is possible to prepare a model animal of a Th2-type disease, and with use of this model animal, it is possible to screen therapeutic agents of Th2-type diseases.

Currently, for treatment of Th2-type allergic diseases caused by Th2 cytokines, compositions aiming for suppressing activity of various chemical transmitters have been used, which chemical transmitters are produced from effector cells (such as mast cells) activated by IgE antibodies and Th2 cytokines. Not much work has been made for development of a therapeutic agent of a Th2-type allergic disease, for suppressing production of the Th2 cytokines themselves.

Known methods of suppressing the production of the Th2 cytokines themselves are to administer a large amount of IL-12 or to administer a combination of IL-12 and IL-18. The in vivo administration of IL-12 and IL-18 gives effect on various cells and induces the production of IFN-γ. This produced IFN-γ exhibits an effect of preventing infection of cytozoic pathogen and further anti-allergy effects. However, the combined administration of IL-12 and IL-18 induces excess production of IFN-γ. This causes excess inflammation reactions; as a result, strong side effects such as hepatotoxin or the like are caused. Hence, the combined administration of IL-12 and IL-18 is inappropriate for use in actual treatment.

The technique of treating and preventing Th2-type diseases such as infectious diseases and allergic diseases, by suppressing the induction of the naive CD4$^+$ T cells which causes development into the Th2 cells and by suppressing the production of Th2 cytokines from the induced Th2 cells, is highly expected as being effective and as having no side effects. However, the nature of the cells that produce early IL-4, which early IL-4 is required for developing the naive CD4$^+$ T cells into the Th2 cells, remain unknown. The working mechanism of the natural immunity cells developing into the Th2 cells has also not been made clear.

The present invention clarified the mechanism of initiating Th2-type immune response. This as a result clarified how to obtain a medicament which suppresses the induction of naive CD4$^+$ T cells to develop into Th2 cells, and how to obtain a medicament which suppress production of Th2 cytokines from the Th2 cells developed by the induction.

The present invention provides a method of screening a therapeutic agent of a Th2-type disease. As described above, basophils internalize and process antigens, and present the processed antigens. Hence, in a case where the surface presentation by basophils is suppressed or inhibited due to the presence of a candidate substance, it can be determined that that candidate substance is effective for treatment of the Th2-type disease.

Namely, in one embodiment, a screening method according to the present invention includes: (a) producing a complex of an antigen and IgE binding to the antigen; (b) culturing basophils in the presence of the complex, the step (b) being carried out in the presence or absence of a candidate substance; and (f) measuring an amount of MHC class II molecules or CD80 molecules presented on a cell surface of the basophils having been subjected to the step (b). It is possible to easily measure the amount of the MHC class II molecules or CD80 molecules presented on the surface of the cells of basophils with use of an antibody of the protein.

Moreover, basophils internalize and process an antigen, and present the processed antigen on its surface, and further produces IL-4. Naive T cells recognize MHC class II molecules/antigen peptide complex presented on the surface of the basophils in the presence of this IL-4, and are induced to develop into Th2 cells. Hence, in the case where the induction to develop into the Th2 cells are suppressed or inhibited due to the presence of the candidate substance, it can be determined that that candidate substance is effective for treatment of the Th2-type disease.

Namely, in one embodiment, a screening method according to the present invention includes the steps of: (a) producing a complex including an antigen and IgE binding to the antigen; (b) culturing basophils in the presence of the complex; (c) culturing naive T cells with the basophils cultured in the step (b), the step (b) or the step (c) being carried out in the presence or absence of a candidate substance; and (g) measuring Th2 cells developed due to the induction in the step (c). The amount of the Th2 cells developed due to the induction can be easily measured by methods such as flow cytometry using a surface marker.

Furthermore, basophils internalize and process an antigen, and present the processed antigen on its surface, and further produces IL-4. Naive T cells recognize a complex presented on the surface of the basophils in the presence of this IL-4, and are induced to develop into Th2 cells. Upon induction to develop into the Th2 cells, B cells produce IgE of the antigen by being effected by the Th2 cells. Hence, in the case where the production of IgE is suppressed or inhibited by the presence of the candidate substance, it can be determined that that candidate substance is effective for treatment of the Th2-type disease.

Namely, in one embodiment, the screening method according to the present invention includes the steps of: (a) producing a complex of antigen and IgE binding to the antigen; (b) culturing basophils in the presence of the complex; (c) culturing naive T cells with the basophils cultured in the step (b); (d) culturing B cells with Th2 cells induced in the step (c), in the presence of the antigen and professional antigen-presenting cells, to produce IgE, at least one of the steps (b) to (d) being carried out in the presence or absence of a candidate substance; and (h) measuring an amount of IgE produced in the step (d). The amount of IgE can be easily measured by use of an anti-IgE antibody.

The IgE measured in the embodiment is what is called early IgE. As described above, the present invention further provides a method of producing secondary IgE. Hence, in a case where production of the secondary IgE is suppressed or inhibited due to the presence of a candidate substance, it can be determined that that candidate substance is effective for treatment of a Th2-type disease.

Namely, in one embodiment, a screening method according to the present invention includes the steps of: (a) producing a complex including an antigen and IgE binding to the antigen; (b) culturing basophils in the presence of the complex; (c) culturing naive T cells with the basophils cultured in the step (b); (d) culturing B cells with Th2 cells induced in the step (c), in the presence of the antigen and professional antigen-presenting cells, to produce IgE; (e) culturing the antigen, the Th2 cells and the B cells in the presence of the IgE produced in the step (d), at least one of the steps (b) to (e) being carried out in the presence or absence of a candidate substance; and (i) measuring an amount of IgE produced in the step (e).

A person skilled in the art who has read the present specification would easily understand that a therapeutic agent for a Th2-type disease can be screened by measuring, with use of a model animal of the Th2-type disease described later, whether or not improvement is attained in a disease. Namely, in one embodiment, a screening method according to the present invention, for screening a therapeutic agent of a Th2-type disease, includes the steps of: culturing basophils in the presence of a complex of an antigen and IgE binding to the antigen; administering to an animal the basophils cultured in the presence of the complex, to prepare a model animal; administering a candidate substance to the model animal; and measuring whether or not improvement is attained of the Th2-type disease, in the model animal to which the candidate substance is administered.

As described above, a composition according to the present invention is usable for preparing a model animal of a Th2-type disease. Namely, a model animal preparation method according to the present invention, for preparing a model animal of a Th2-type disease, includes: culturing basophils in the presence of a complex of an antigen and IgE binding to the antigen; and administering to an animal the basophils cultured in the presence of the complex. It is preferable that the Th2-type disease is selected from the group consisting of: hay fever, bronchial asthma, atopic dermatitis, allergic enteritis, allergic conjunctivitis and allergic rhinitis. A model animal prepared by the preparation method according to the present invention may be a model animal having bronchial asthma, and in this case, it is preferable that the basophils cultured in the presence of the complex is administered by transnasal administration.

The method of preparing the model animal according to the present invention requires no adjuvant. Although many of model animals have been prepared of the Th2-type disease, there is no case where the model animal is prepared without using an adjuvant.

2: Antigen-IgE Complex and Use Thereof.

As described above, the inventors of the present invention found that basophils induce Th2 response. Simultaneously to this, the inventors found that a similar Th2 response is induced by transferring an antigen-IgE complex to normal mice. More specifically, as described in Examples later described, Th2 cells are promptly induced in spleens of mice immunized with basophils that are cultured with DNP-OVA/anti-DNP IgE complex. Moreover, in naive mice into which a DNP-OVA/anti-DNP IgE complex is injected, production of early IL-4 is induced in peripheral blood, spleen, and bone marrow of the naive mice; and in the spleen of the mice into which an IgE complex is injected, the Th2 cells are promptly induced. On the other hand, in spleens of basophils-depleted mice (MAR-1 processed mice) into which a DNP-OVA/anti-DNP IgE complex is injected, no Th2 cells are induced. These points indicate not only that the basophils produce early IL-4 and thereafter induce Th2 response, it also indicates that the complex of an antigen and IgE binding to the antigen serves as an initial stimulatory substance in production of early IL-4 with basophils. More specifically, the new finding by the inventors of the present invention is of an induction of Th2 response by basophils, and further an induction of Th2 response by a complex of IgE and its antigen. As such, the present invention is accomplished based on a new finding that cannot be easily perceived by a person skilled in the art.

Namely, the present invention provides a complex of an antigen and IgE binding to the antigen. Use of the complex according to the present invention allows for production of early IL-4 from the basophils, thereby making it possible to induce naive T cells to develop into Th2 cells, produce secondary IL-4, and produce IgE of the antigen. Furthermore, use of the complex according to the present invention allows for screening a therapeutic agent for a Th2 disease and for preparing a Th2-type disease model animal.

Generally, an immune complex made up of an antigen and its antibody is formed under conditions in which a large amount of antibodies are present. Hence, an extremely high blood level of IgG or IgM can be observed in vivo. Although IgE is one type of immunoglobulin, IgE has an extremely low blood level as compared to IgG and IgM. Accordingly, IgE binding to the antigen in vivo is already bound to basophils or mast cells via its Fc region. Namely, it is thought that in the living body, the antigen-IgE complex is not present inside blood, but is present as a complex of an antigen-IgE-cell, and that it is the complex of the antigen-IgE-cell that is involved with allergic reaction.

The complex according to the present invention is made up of an antigen and IgE binding to the antigen, and the Fc region of the IgE is bound to no cell (e.g., basophils and mast cells). From this point of view, the complex according to the present invention can be said as to be a complex free from cells (free complex).

As such, the complex made up of IgE and its antigen is not recognized in the technical field. Furthermore, the fact that such a complex serves for the production of early IL-4 from basophils is not only unknown until now, but is completely unpredictable by a person skilled in the art.

As described above, hapten may be connected to the antigen, to accelerate the formation of an antigen-IgE complex that is to be internalized into the basophils. In this case, IgE can be an anti-hapten IgE; in the present specification, the anti-hapten IgE is also included in the scope of the IgE binding to the antigen.

Furthermore, the present invention provides a composition and a kit, each for forming the free complex. Since the composition and kit according to the present invention allows for forming the free complex, it is possible to produce early IL-4 from basophils; as a result, it becomes possible to induce naive T cells to develop into Th2 cells, produce secondary IL-4, and produce IgE of an antigen. Furthermore, use of the composition and kit according to the present invention allows for screening a Th2 disease therapeutic agent and for preparing a Th2-type disease model animal.

Namely, the composition and kit according to the present invention can be a composition and a kit each used for producing early IL-4 from basophils, can be a composition and a kit for inducing naive T cells to develop into Th2 cells, can be a composition and a kit for producing secondary IL-4, can be a composition and a kit for producing IgE of an antigen, can be a composition and a kit for screening a Th2 disease therapeutic agent, and can be a composition and a kit for preparing a Th2-type disease model animal.

The composition according to the present invention includes an antigen and IgE binding to the antigen. Since the object of the present invention is to cause formation of a complex made up of an antigen and IgE binding to the antigen, it is preferable that the composition according to the present invention includes no cells which can bind to a Fc region of IgE (e.g., basophils). The antigen and IgE included in the composition according to the present invention may be made into a complex or may be not made into a complex. Even if the composition is not made into a complex, it is extremely high in possibility that IgE in the composition binds with the antigen also in the composition, before the IgE has the chance to bind to cells in the living body. This is because IgE and its antigen are made present within a limited space, i.e., the composition, and are provided into a living body in that state. This significantly leads to attain the effect of the present invention. Note that a mode of the composition according to the present invention may be a kit which independently includes an antigen and IgE binding to the antigen; as long as the antigen and IgE are made existing in a limited space, there is no limitation in its mode. That is to say, the composition according to the present invention may be of any mode as long as an antigen-IgE complex is obtained before the binding of IgE-cells is achieved in vivo.

The kit according to the present invention includes: an antigen; IgE binding to the antigen; and basophils. Since an object of the kit is to form the free complex, as long as IgE and cells are sufficiently included independently in the kit according to the present invention, the kit may be of a mode in which an antigen, IgE binding to the antigen, and basophils are included independently from each other, or alternatively, the kit may be of a mode in which a composition including an antigen and IgE binding to the antigen and basophils are included independently. The kit according to the present invention may also be any kit as long as it provides an antigen and IgE binding to the antigen to a living body in a state in which both the antigen and IgE are present within a limited space; the kit may be in any mode as long as it can have an antigen-IgE complex be obtained before the IgE is bound to a cell in the living body.

Note that it would be easy for a person skilled in the art who has read the present specification to understand that the following methods, each of which use a free complex (antigen-IgE complex) according to the invention, can all be carried out according to the description in the foregoing "Basophils and its use": the method of inducing naive T cells to develop into Th2 cells; the method of producing IL-4; the method of producing IgE; the method of screening a therapeutic agent of a Th2 disease; and the method of preparing a model animal of a Th2-type disease.

3: Further Use

As described above, the inventors of the present invention demonstrated that antigen presentation by endogenous basophils is critically important to the induction of early Th2 response. Furthermore, the inventors of the present invention demonstrated that the induction of Th2 cells development is inhibited by depleting basophils in a living body. Namely, the present invention provides a technique for treating Th2-type diseases. The wording "treatment" used in the present specification denotes alleviation or elimination of symptoms, and includes both of preventive (before development of symptoms) and therapeutical (after development of symptoms) treatment. The expression "treat a Th2-type disease" denotes to suppress or inhibit the induction of Th2 cells development. It is preferable that the induction of Th2 cells development be suppressed to a degree that symptoms of the Th2-type disease is relieved, and it is further preferable that the induction of the Th2 cells development be suppressed to a degree in which the symptoms of the Th2-type disease are eliminated (i.e., the disease cures).

The present invention provides a composition for treatment of a Th2-type disease. As described above, it is possible to carry out treatment of a Th2-type disease by depleting basophils from a subject. Namely, a composition according to the present invention may be any composition as long as it contains a substance which causes depletion of basophils. It is preferable that an antibody of FcεR1 is used as such a substance. Moreover, the antibody of FcεR1 can be said as a substance which inhibits functions of FcεR1 (for example, inhibits binding with FcεR1). That is to say, the composition according to the present invention may include a substance which inhibits a function of FcεR1. A mode of the composition according to the present invention is preferably a mode in which basophils can be depleted in blood or in peripheral tissues, i.e., in an injectable mode. However, the mode is not limited to this. The composition according to the present invention may be provided in a mode of a kit as described above. In other words, the present invention provides a kit for use in treatment of a Th2-type disease. Either the mode of a composition or the mode of a kit, a person skilled in the art would possibly be able to appropriately select components other than active components in the present invention.

The present invention also provides a method for treating a Th2-type disease. The method according to the present invention may be a method using the aforementioned composition, i.e., may be any method as long as the method includes depleting basophils from a subject, or administering to a subject a substance which inhibits a function of FcεR1. The method according to the present invention may be used for prevention or for treatment. Moreover, administration modes and administration paths are also not particularly limited.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Moreover, all academic literatures and patent literatures mentioned in the present specification are incorporated as reference in the present specification.

EXAMPLES

1. Materials and Methods

Mice

BALB/c mice were purchased from Jackson Laboratory. Mice transgenic for αβTCR recognizing $OVA_{323-339}$ (DO11.10) and BALB/c G4-homozygous (IL-4-deficient) mice were mated in SPF conditions at the animal facilities of Hyogo College of Medicine. All animal experiments were done in accordance with guidelines of the Institutional Animal Care Committee of Hyogo College of Medicine.

Cell Purification

Mouse bone marrow-derived basophils and mast cells were prepared in accordance with previous reports (Kondo, Y. et al. Int Immunol 20, 791-800 (2008) and Yoshimoto, T. et al. Proc Natl Acad Sci USA 96, 13962-6 (1999)). Purity of each population was over 96%. Further information and descriptions regarding purification of human basophils and mouse $CD4^+$ $CD62L^+$ resting T cells are described later.

In Vitro Culture

Naive splenic $CD4^+$ $CD62L^+$ T cells ($1 \times 10^5$ cells per mL) from DO11.10 mice were stimulated for 7 days in 48-well plates with IL-2 (100 pM), IL-3 (20 U/mL), and $OVA_{323-339}$ (1 μM) or DNP-OVA (6.25 to 100 μg/mL), in the presence of conventional APCs (irradiated T cell-depleted BALB/c splenocytes), irradiated splenic DCs, irradiated purified basophils, or purified mast cells ($5 \times 10^5$ cells per mL each). For the induction of Th2 cells, IL-4 (1000 U/mL) was also added to the culture. After initial priming, cells were washed, then were again cultured for 4 hours with PMA (50 ng/mL) plus ionomycin (500 ng/mL) and were analyzed by FACS for cytosolic IL-4 and IFN-γ. In some experiments, after initial priming, $CD4^+$ T cells ($1 \times 10^5$ per 0.2 mL per well) were restimulated for 48 hours in 96-well plates with IL-2 (100 pM) and $OVA_{323-339}$ (1 μM), in the presence of irradiated conventional APCs ($1 \times 10^5$). Supernatants were collected and cytokine production was assessed with ELISA kits (R&D Systems) or the Bio-Plex system (BioRad).

Parasites

BALB/c mice were subcutaneously inoculated with 5,000 *S. venezuelensis* third-stage larvae to initiate complete infection.

Statistics

Data are given as mean±s.e.m. Statistical comparisons between two experimental groups were made with a paired Student's t-test using GraphPad Instat Software. P values of less than 0.05 were considered as significantly different.

Antibodies and Reagents

Anti-mouse IL-4 (11B11) was purified in the inventors' laboratory. PE-anti-mouse CD4, FITC-anti-mouse CD62L, FITC-anti-mouse I-A$^d$, FITC-anti-mouse CD40, FITC-anti-mouse CD80, FITC-anti-mouse CD86, FITC-anti-mouse CD11c, PE-anti-mouse c-kit, FITC-anti-mouse c-kit, FITC-anti-mouse DX5, FITC-anti-human HLA-DR, and APC-anti-human CD203a were purchased from BD Biosciences. FITC-anti-mouse T1/ST2 (DJ8), biotin-anti-mouse Fcε1α (MAR1), streptavidin-PE, and streptavidin-APC were purchased from eBioscience. The following PE-labeled anti-human mAbs were purchased from BD Biosciences: anti-CD3, anti-CD7, anti-CD14, anti-CD15, anti-CD16, anti-CD19, anti-CD36, anti-CD45RA and anti-CD235a. Recombinant mouse IL-2, IL-3, IL-4 and human IL-3 were purchased from R&D Systems. IL-18 was purchased from MBL. Recombinant human IL-33 was purified in the inventors' laboratory. Anti-DNP IgE mAB, OVA (grade V), LPS from *Salmonella minnesota* Re-595 or *E. coli* O55:B5, and PGN from *Staphylococcus aureus* were purchased from Sigma. OVA-DNP was prepared according to a method disclosed in Eisen, H. N. et al. J Immunol 73, 296-308 (1954).

Flow Cytometry and Cell Purification

For the preparation of bone marrow-derived basophils, bone marrow cells were cultured for 14 days with IL-3 (10 U/mL) in RPMI 1640 supplemented with 10% FBS, 2-ME (50 µM), L-glutamine (2 mM), penicillin (100 U/mL) and streptomycin (100 µg/mL), and were washed twice. Cells were first treated for 30 minutes at 4° C. with anti-FcγRII/III (10 µg/mL), followed by treatment for 1 hour at 4° C. with biotin-anti-mouse FcεR1α (5 µg/mL) in staining buffer (PBS, 1% FBS). After being washed twice, cells were stained for 30 minutes with streptavidin-APC and PE-anti-mouse c-kit. Samples were analyzed on a FACS Calibur (BD Biosciences) and were separated into FcεR1$^+$/c-kit$^-$ cells (basophils) and FcεR1$^+$/c-kit$^+$ cells (mast cells) with a fluorescence cell sorter (FACS Aria; BD Biosciences). The resultant populations were further stained with FITC-labeled antibodies for analysis of surface markers. For preparation of splenic basophils, spleen cell samples from BALB/c mice were first depleted of Thy1.2$^+$ T cells and B220$^+$ cells with a MACS system (MiltenyiBiotec), then the residual cells were further stained and separated into FcεR1$^+$/c-kit$^-$ cells and FcεR1$^+$/c-kit$^+$ cells with a FACS Aria. The purity of each population was over 96%. For the preparation of splenic CD4$^+$ CD62L$^+$ resting T cells and for intracellular cytokine staining, the following procedures were carried out.

Human peripheral blood from normal volunteers and umbilical cord blood obtained from normal full-term deliveries were obtained and processed, after informed consent was given. The Institutional Review Board approved the experimental plan. Mononuclear cells were isolated from the peripheral blood and cord blood by Ficoll density-gradient centrifugation. Peripheral blood mononuclear cell samples were further depleted of T cells, monocytes, eosinophils, natural killer cells, B cells, platelets, DCs and erythroid cells with a 'cocktail' of PE-labeled monoclonal antibodies to human CD3, CD7, CD14, CD15, CD16, CD19, CD36, CD45RA and CD235a and anti-PE MicroBeads (Miltenyi-Biotec). Umbilical cord blood mononuclear cells were further enriched to CD34$^+$ cells with MicroBeads. These CD34$^+$ progenitor cells were plated at a density of $5 \times 10^5$ cells per mL in 12-well plates and were cultured for 7 days in STEM PRO-34 SFM medium (GIBCO) supplemented with 10% FBS, 2-ME (50 µM), L-glutamine (0.5 mM), penicillin, (50 U/mL), streptomycin (50 µg/mL) and human IL-3 (10 ng/mL).

Electron Microscopy

Sorted mouse bone marrow-derived cells (FcεR1$^+$/c-kit$^-$ cells and FcεR1$^+$/c-kit$^+$ cells) and human cells (CD203c+ HLA-DR cells) were fixed with 2% paraformaldehyde and 1.25% glutaraldehyde, were post-fixed with 1% OsO$_4$ and were embedded in Epon. Ultrathin sections were double-stained with uranyl acetate and lead citrate and were examined with a JEM 1220 transmission electron microscopy (JEOL).

Proliferation Assay

Naive splenic CD4$^+$ CD62L$^+$ T cells from DO11.10 mice ($5 \times 10^4$ cells per 0.2 mL per well) were stimulated for 4 days in 96-well plates with IL-2 (100 pM), IL-3 (20 U/mL), and OVA$_{323-339}$ (1 µM) or DNP-OVA (6.25 to 100 µg/mL) with or without monoclonal anti-DNP IgE (10 µg/mL), in the presence of conventional APCs or purified basophils ($2.5 \times 10^5$ cells per mL each). DNA synthesis was assessed by measurement of the incorporation of 1 µCi [$^3$H] thymidine during the final 16 hours.

ELISA Assay

OVA-specific serum IgE was measured with a Mouse OVA-IgE ELISA kit (Dainippon Sumitomo Pharma Co., Ltd.). OVA-specific serum IgG1 was measured with a Mouse OVA-IgG1 ELISA kit (AKRIE-04, Shibayagi).

In Vivo Treatment of Mice

Bone marrow-derived and FACS sorted basophils and mast cells ($5 \times 10^5$ cells per mL each) were cultured for 16 hours in 48-well plates with IL-3 (20 U/mL), DNP-OVA (100 µg/mL) and anti-DNP IgE mAb (10 µg/mL). After priming, the basophils or mast cells (2.5 to $5 \times 10^5$ cells per mouse) were transferred through the tail vein into BALB/c mice (5 mice per group). At 4 days or 1 week after reconstitution, the mice were intravenously challenged with OVA protein (100 µg) in PBS. In some experiments, BALB/c mice (5 mice per group) were injected intravenously with a mixture of DNP-OVA (100 µg per mouse) and anti-DNP IgE mAb (200 µg per mouse). After injection, expression of GFP as a reporter of IL-4 was measured over time with FACS, to measure expression of IL-4 in the basophils. For in vivo depletion of basophils, a method of Denzel et al. was followed. The mice were injected intraperitoneally twice daily for 3 days with 5 µg anti-mouse FcεR1α (MAR-1) or control hamster IgG (eBioscience). Mice were allowed to 'rest' for 2 days and then were injected with a mixture of DNP-OVA and anti-DNP IgE mAb. Thereafter, these mice were injected twice daily for an additional 3 days with MAR-1 or hamster IgG. Four days after injection of DNP-OVA and anti-DNP IgE, splenic CD4$^+$ cells ($1 \times 10^5$ cells per 0.2 mL per well) were stimulated for 5 days in 96-well plates with IL-2 (100 pM) and OVA (100 µg/mL) in the presence of $1 \times 10^5$ irradiated conventional APCs. Splenic CD4$^+$ T cells were stimulated for 5 days with PVA-pulsed APC.

Analysis of Expression of TLR mRNA

Total RNA was extracted from the sorted basophils and mast cells with Trizol reagent, was treated with DNase I and was reverse-transcribed with Superscript II RT and oligo (dT)$_{12-18}$ primer (Invitrogen). As a positive control for each TLR, RNA extracted from total spleen cells was used. For analysis of expression of TLR mRNA, mRNA was amplified by a modified standard RT-PCR amplification procedure. The specific TLR primer sequences and their annealing temperatures were set. cDNAs were amplified for 35 cycles, each composed of 95° C. for 30 seconds, 55° C. for 30 seconds, and 72° C. for 30 seconds, and then further extension at 72° C. for 10 minutes. After carrying out 35 cycles, the samples were stored at 4° C. until analysis. After amplification, PCR products were separated by electrophoresis through 1.7% agarose gels and were visualized by illumination with UV light illumination.

2. Results and Studies

The inventors of the present invention demonstrated the contribution of basophils to Th2-IgE response in vitro and in vivo, by producing IL-4 and presenting MHC class II/peptide complex to naive CD4+ cells.

First examined was the ability of splenic basophils to produce Th2 cytokines and to induce development of naive CD4+ T cells into Th2 cells in vitro. Non-T cell, non-B cell fractions from naive mice contained 0.20% FcεR1+/c-kit− cells, whereas those from mice infected with *Strongyloides venezuelensis* (*S. venezuelensis*-infected mice) had a much greater proportion of these cells (5.84%; FIG. 1(*a*)), as reported for mice infected with the parasite *Nippostrrongylus brasiliensis* (*N. brasiliensis*). FcεR1+/c-kit− cells (basophils) were purified from the spleens of naive mice and infected mice. Splenic basophils from the infected mice cultured for 24 hours in the presence of IL-3 produced large amounts of IL-4, IL-6, and IL-13, however did not produce IL-12. Meanwhile, splenic basophils from the naive mice produced small amounts of IL-4, IL-6, and IL-13, in response to IL-3. This result suggests that the splenic basophils from infected mice gain an ability to strongly produce IL-4, IL-6, and IL-13, in a culture including IL-2 (FIG. 1(*b*)).

Next examined was the ability of basophils from the infected mice, to induce OVA-specific naive CD4+ T cells to develop into Th2 cells in the presence of OVA peptide ($OVA_{323-339}$), IL-2 and IL-3. Moreover, naive CD4+ T cells were cultured with conventional APCs (T cell-depleted splenic cells), in the presence of $OVA_{323-339}$ and IL-2. Splenic basophils from *S. venezuelensis*-infected mice exhibited a notable ability to induce naive CD4+ T cells to develop into Th2 cells in the absence of IL-4 (FIG. 1(*c*)). In contrast, as reported elsewhere, conventional APCs failed to induce naive CD4+ T cells to develop into the Th2 cells in the Th0 conditions ($OVA_{323-339}$ and IL-2 only) (FIG. 1(*c*)). The developed Th2 cells expressed Th2 marker IL-33Rα (FIG. 1(*d*)), produced Th2 cytokines when challenged with OVA, and increased their production of Th2 cytokines other than IL-4 when challenged with antigen plus IL-33.

Figure 6:
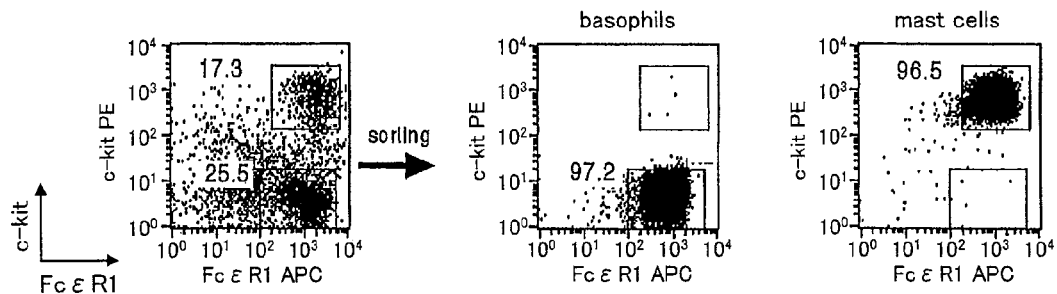
FIG. 6(a) is a view showing a result obtained after carrying out the following procedures: culture bone marrow cells from mice with IL-3 for 10 days; analyze this cultured bone marrow cells for expression of FcεR1 and c-kit by flow cytometry; and sort the analyzed bone marrow cells into cell population of FcεR1$^+$/c-kit$^-$ (basophils) and cell population of FcεR1$^+$/c-kit$^+$ (mast cells), by FACS Aria.
FIG. 6(b) is a view showing a result of observing the sorted cell populations of FcεR1$^+$/c-kit$^-$ (basophils) and FcεR1$^+$/c-kit$^+$ (mast cells), by electron microscopic examination.
FIG. 6(c) is a view showing a result of measuring expression of HLA-DR and CD203c, of negative enriched human peripheral blood mononuclear cells, immediately after the selection (left) or after culturing for 24 hours in the presence of human IL-3 (right).
FIG. 6(d) is a view showing a result of sorted CD203c$^+$/HLA-DR$^+$ cell populations being subjected to Wright-Giemsa staining (left; 100×) and being subjected to electron microscopic examination (right).
Figure 6:
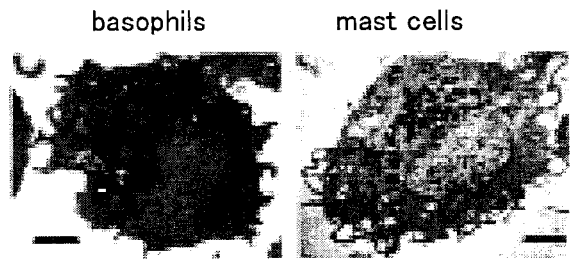
Figure 6:
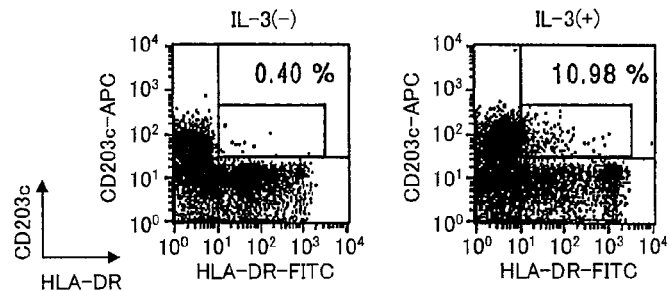
Figure 6:
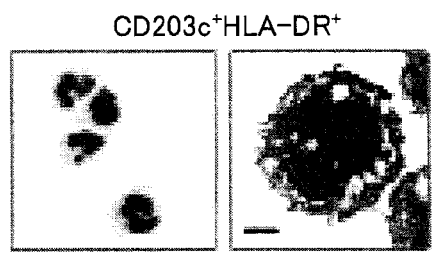

To avoid potential contamination of splenic basophils with DCs, the ability of highly purified bone marrow basophils to induce Th2 cells development in vitro (FIG. 6(*a*), FIG. 6(*b*)) were examined. First examined was their expression of MHC class II molecules and the co-stimulatory molecules CD80 and CD86. Simultaneously, the expression of these molecules by mast cells and conventional APCs were examined (FIG. 2(*a*)). Bone marrow-derived basophils and conventional APCs expressed class II molecules, CD80 and CD86 but not CD11c. In contrast, the mast cells express these molecules modestly (FIG. 2(*a*), FIG. 2(*b*)). Splenic basophils express CD62L (lymph node-homing molecule), which suggests their potential to enter into lymphoid tissues. Human basophils (CD203c±/c-kit−) derived from cord blood or peripheral blood also express HLA-DR (FIG. 2(*c*), FIG. 6(*c*), FIG. 6(*d*)).

Figure 3:
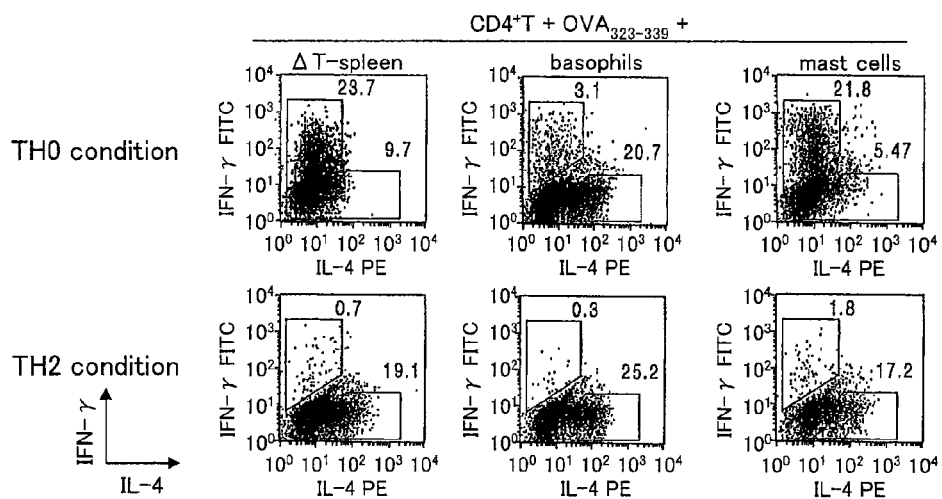
FIG. 3(a) is a view showing a result of analysis by FACS for expression of IL-4 and IFN-γ in CD4$^+$ T cells produced by stimulating naive T cells with OVA$_{323-339}$ in the presence of T cell-depleted mice splenocytes (ΔT-spleen) or bone marrow-derived purified basophils or mast cells. For induction to develop into Th2 cells, IL-4 (1000 U/mL) was further added to the culture (Th2 condition).
FIG. 3(b) is a view showing a result of analysis by FACS for expression of IL-4 and IFN-γ in CD4$^+$ T cells produced by stimulating naive T cells with OVA$_{323-339}$ in the presence of bone marrow-derived purified basophils (WT: wild type; G4/G4: IL-4-deficient mice), or splenic DC.
FIG. 3(c) is a view showing a result of analysis by FACS for expression of IL-4 and IFN-γ in CD4$^+$ T cells produced by stimulating naive T cells with DNP-OVA in the presence of the T cell-depleted mice splenocytes (ΔT-spleen) or bone marrow-derived purified basophils.
FIG. 3(d) is a view showing a result of analysis by FACS for expression of IL-4 and IFN-γ in CD4$^+$ T cells produced by stimulating naive T cells with DNP-OVA (6.25~100 µg/mL) with or without anti-DNP IgE mAb in the presence of T cell-depleted mice splenocytes (ΔT-spleen) or bone marrow-derived purified basophils.
Figure 3:
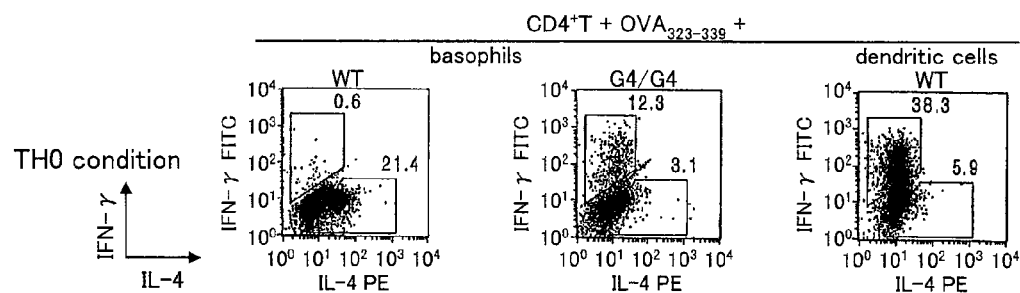
Figure 3:
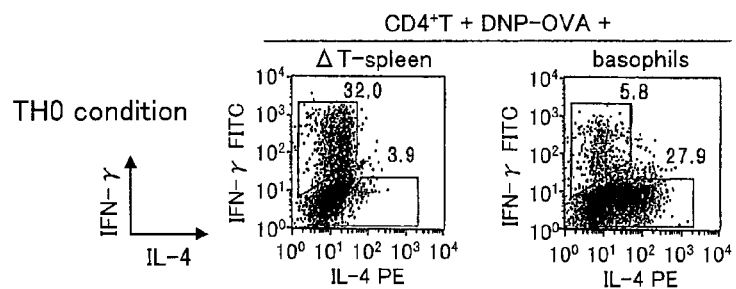
Figure 3:
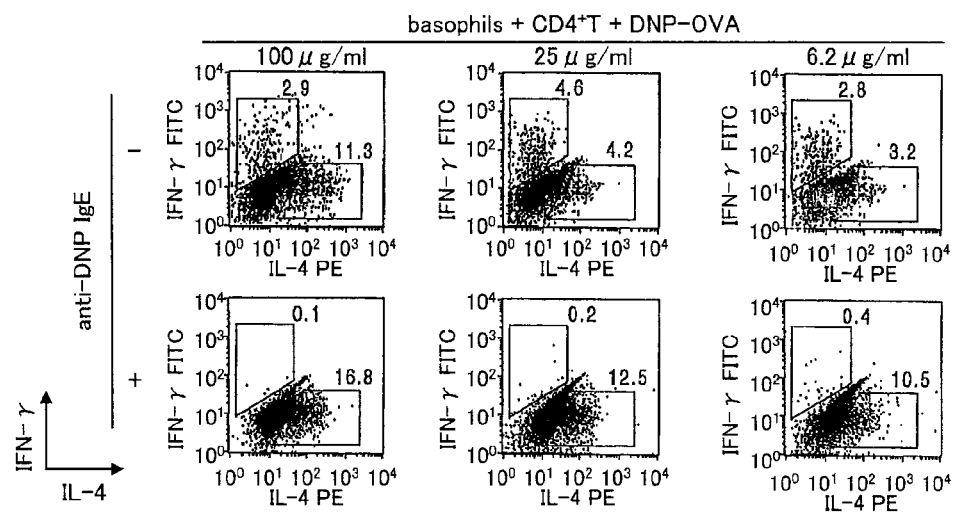

Expectedly, like splenic basophils from *S. venezuelensis*-infected mice, bone marrow-derived basophils, even in the complete absence of professional APCs, have the ability to induce naive CD4+ T cells to develop into Th2 cells under this Th0 condition ($OVA_{323-339}$, IL-2 and IL-3, without IL-4) (20.7%)(FIG. 3(*a*)).

Examination of the mechanism of how basophils induce the Th2 cell development was carried out. When naive CD4+ T cells were stimulated with $OVA_{323-339}$, conventional APCs (ΔT-spleen), IL-2, and IL-4 (under Th2 condition), the naive CD4+ T cells developed into Th2 cells (19.1%) (FIG. 3(*a*)). Similarly, when naive CD4+ T cells were stimulated with $OVA_{323-339}$, mast cells, IL-2, IL-3 and IL-4 (under Th2 condition), the naive CD4+ T cells developed into Th2 cells (17.2%) (FIG. 3(*a*)). In contrast, an additional IL-4 stimulation (under Th2 condition) only modestly enhanced this basophils-dependent Th2 cell development (25.2%; FIG. 3(*a*)). Furthermore, basophils from IL-4-deficient mouse almost completely abolished this Th2 development (3.1%), while wild-type basophils but not professional APCs induced naive CD4+ T cells into Th2 cells under the Th0 condition (FIG. 3(*b*)). These results taken together indicate that basophils produce IL-4 and present OVA peptide, and that basophils induce naive CD4+ T cells to develop into Th2 cells.

Next, DNP-conjugated OVA (DNP-OVA) was used as an antigen instead of OVA peptide ($OVA_{323-339}$). It was possible to induce OVA-specific Th2 cells by culturing OVA-specific naive CD4+ T cells with basophils in the presence of IL-3 and DNP-OVA and absence of IL-4 (FIG. 3(*c*)). These results suggest that basophils have the ability to internalize and to process native OVA into $OVA_{323-339}$ and display peptide fragment in association with MHC class II and produce IL-4. Next examined was whether addition of anti-DNP IgE monoclonal antibody can up-regulate APC ability of basophils (FIG. 3(*d*)). OVA-specific naive CD4+ T cells were cultured for 7 days with basophils in the presence of 100 µg/ml, 25 µg/ml, or 6.2 µg/ml of DNP-conjugated OVA and 10 µg/ml of anti-DNP-IgE monoclonal antibody. After culturing, the cells were thoroughly washed, and were cultured in the presence of PMA+ionomycine for 4 hours. Thereafter, expression of IL-4 and IFN-γ within the cytoplasm was measured by FACS. The numbers indicate proportions of cells in the CD4+ T cells which include IL-4 or IFN-γ within the cytoplasm. Basophils pulsed with a low dose (6.2 µg/mL) of DNP-OVA modestly induced Th2 cells (3.2%), whereas pulsation with a higher dose (100 µg/mL) of DNP-OVA markedly induced the Th2 cells (11.3%). The addition of anti-DNP IgE monoclonal antibody significantly induced the Th2 cells (without anti-IgE: 3.2%, 4.2%, 11.3%, versus with anti-IgE: 10.5%, 12.5%, 16.8%, respectively; FIG. 3(*d*)). Thus, the enhancing effect of anti-DNP-IgE monoclonal antibody on basophils-induced Th2 cell development is most apparent when basophils are pulsed with low concentrations of DNP-OVA. Furthermore, comparing to professional APCs, a low number of basophils induced naive CD4+ T cells to develop into Th2 cells, under the Th2 condition using anti-DNP IgE monoclonal antibody (FIG. 3(*d*)).

Figure 7:
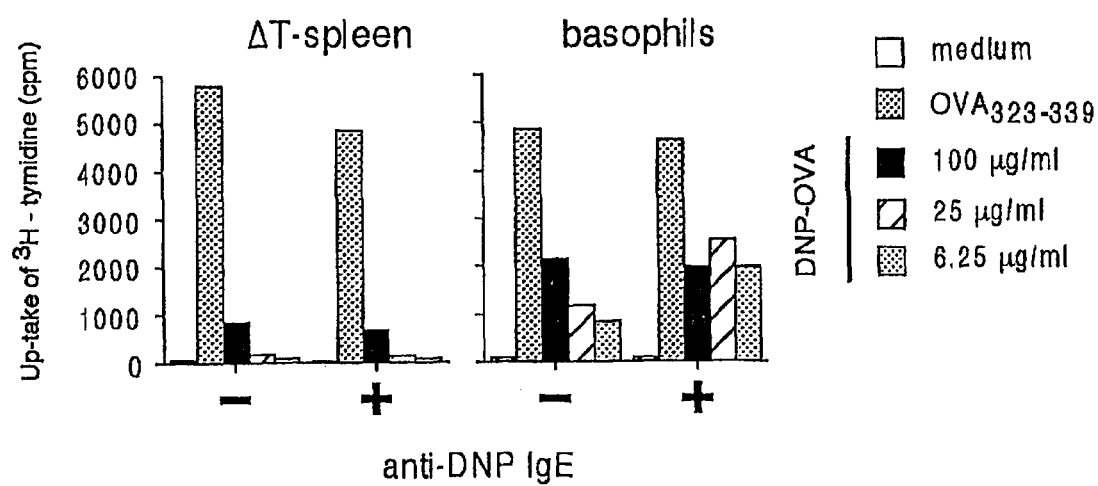
FIG. 7 is a view showing basophils-induced antigen-specific T cell proliferation. Naive T cells were stimulated with OVA$_{323-339}$ (1 μM) or DNP-OVA with or without anti-DNP IgE mAb, in the presence of irradiated ΔT-spleen or basophils for 4 days.
Figure 8:
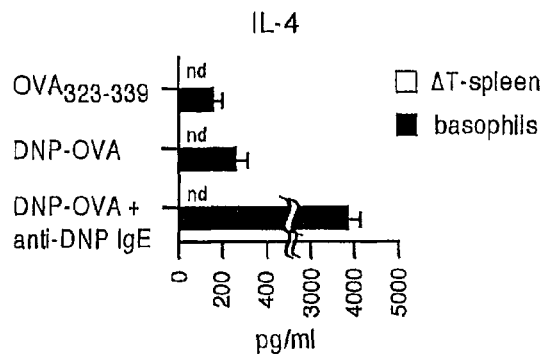
FIG. 8(a) is a view showing a testing result of IL-4 production by ELISA, in which naive T cells are stimulated with OVA$_{323-339}$, or DNP-OVA with or without anti-DNP IgE mAb for 24 hours, in the presence of irradiated ΔT-spleen or basophils. Supernatants thereof were harvested for the testing.
FIG. 8(b) is a view showing a testing result of IL-4 or IL-13 production by ELISA, in which bone marrow-derived and FACS sorted basophils or mast cells are stimulated with DNP-OVA with or without anti-DNP IgE mAb for 16 hours. Supernatants thereof were harvested for the testing.
FIG. 8(c) is a view showing a result of analysis by RT-PCR of mRNAs extracted from bone marrow-derived and FACS sorted basophils or mast cells, for TLR gene and β-actin expression.
FIG. 8(d) is a view showing a testing result of IL-4, IL-6, or IL-13 production by ELISA, in which bone marrow-derived and FACS sorted basophils or mast cells were stimulated with IL-3, and IL-18, IL-33, LPS, or PGN for 24 hours. Supernatants thereof were harvested for the testing.
Figure 8:
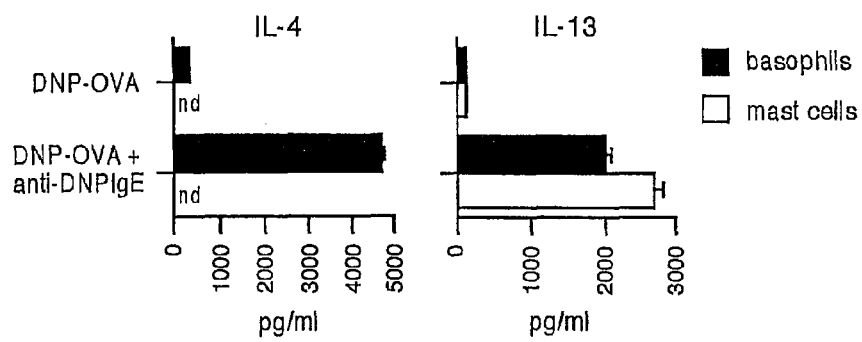
Figure 8:
Figure 8:
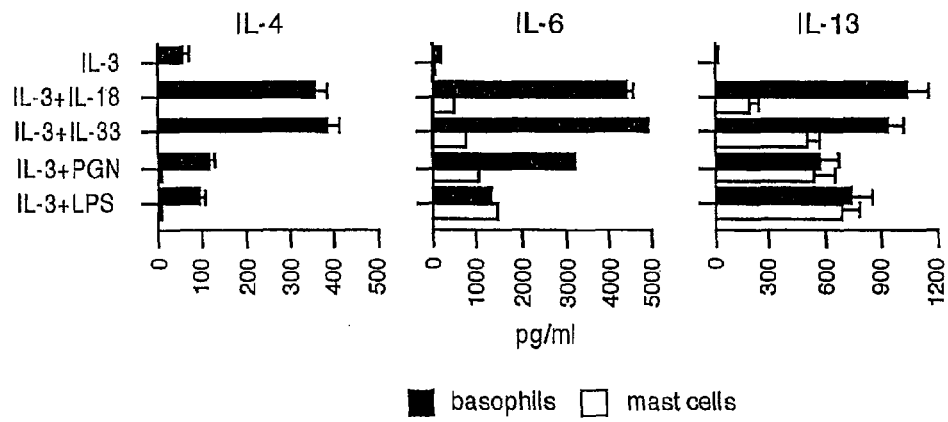

Subsequently, how anti-DNP IgE monoclonal antibody showed this up-regulatory effect was examined. Basophils pulsed with DNP-OVA in the presence of anti-DNP-IgE had a significantly greater ability to induce proliferation of OVA-specific T cells, particularly when basophils were pulsed with a low concentration of DNP-OVA (FIG. 7). In contrast, conventional APCs pulsed in the presence of the anti-DNP-IgE antibodies did not have a greater ability to induce T cell proliferation (FIG. 7). Furthermore, as reported previously, basophils had a much greater ability to produce IL-4 after being pulsed with DNP-OVA in the presence of anti-DNP-IgE antibodies (FIG. 8(*a*), FIG. 8(*b*)). In contrast, mast cells pulsed with DNP-OVA/anti-DNP IgE produced only IL-13, and no IL-4 (FIG. 8(*b*)). Furthermore, only basophils produce IL-4 when stimulated with IL-3 plus IL-18, IL-33, PGN or LPS (FIG. 8(*c*), FIG. 8(*d*)).

To examine whether OVA-pulsed basophils can induce Th2 responses in vivo, attempts were made to heavily pulse basophils with OVA peptide by culturing with a complex of DNP-OVA/anti-DNP IgE. Simultaneously, mast cells were treated with this antigen/antibody complex. Then, these basophils or mast cells were transferred into normal mice through the tail vein of the normal mice. Four days later, the mice were challenged with intact OVA protein dissolved in PBS. Two days after the challenge, splenic CD4$^+$ cells were prepared, and these cells were stimulated with OVA-pulsed APC (ΔT-spleen). Thereafter, IL-4, IL-13, and IFN-γ contents in the culture supernatant were measured. In the spleen, just the OVA-pulsed basophils promptly and strongly induced Th2 cells and modestly induced Th1 cells (FIG. 4($a$)). Next examined was the ability of mice immunized with OVA-pulsed basophils to produce IgE and IgG1 upon intravenous OVA challenge. The systematic administration of OVA without using an adjuvant did not induce IgE response in naive mice. In contrast, mice primed with OVA-pulsed basophils produced IgE and IgG1 in response to the OVA challenge (FIG. 4($b$)). These mice developed CD4$^+$ CD62L$^{low}$IL33Rα$^+$ Th2 cells in their spleens (FIG. 4($c$), FIG. 4($d$)). Since CD62L molecules are markers of recirculating Th2 cells, OVA-pulsed basophils, like professional APCs, induce OVA-specific Th2 cells. These OVA-specific Th2 cells help OVA-activated B cells to produce IgG1 and IgE in vivo.

Figure 9:
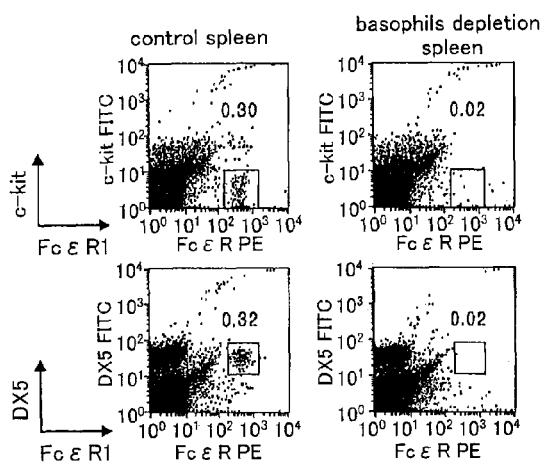
FIG. 9(a) is a view showing a result of quantifying the number of basophils by flow cytometry in spleen of mice intraperitoneally injected with anti-mouse Fcε1α (MAR-1 (+)) or PBS(MAR-1(−)), which spleen is prepared two days after the last injection.
FIG. 9(b) is a view showing a result of quantifying the number of basophils by flow cytometry in liver of mice intraperitoneally injected with anti-mouse Fcε1α (MAR-1(+)) or PBS(MAR-1(−)), which liver is prepared 2 days after the last injection.
FIG. 9(c) is a view showing a result of quantifying the number of basophils in blood prepared from mice that were: intraperitoneally injected with anti-mouse Fcε1α (MAR-1 (+)) or PBS(MAR-1(−)); injected with DNP-OVA/anti-DNP IgE together with MAR-1 or PBS for another 3 more days; intraperitoneally challenged with OVA; and further processed with MAR-1 or PBS.
FIG. 9(d) is a view showing a result of quantifying the number of basophils in spleen prepared from mice which were: intraperitoneally injected with anti-mouse Fcε1α (MAR-1(+)) or PBS(MAR-1(−)); injected with DNP-OVA/anti-DNP IgE together with MAR-1 or PBS for another 3 more days; intraperitoneally challenged with OVA; and further processed with MAR-1 or PBS.
FIG. 9(e) is a view showing a proportion of FcεR1$^+$/DX5$^+$ cells gated on splenic non-B, non-T cells, for frequency of basophils from mice injected with IL-3.
Figure 9:
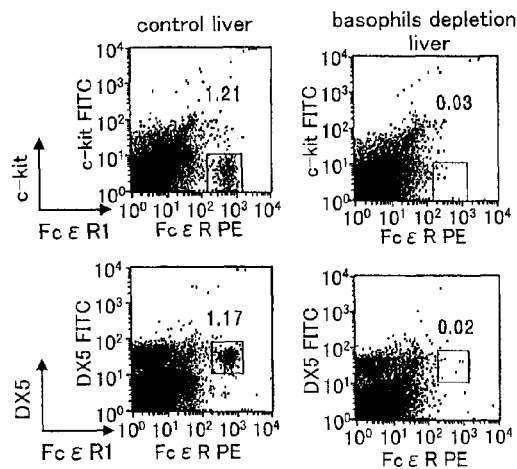
Figure 9:
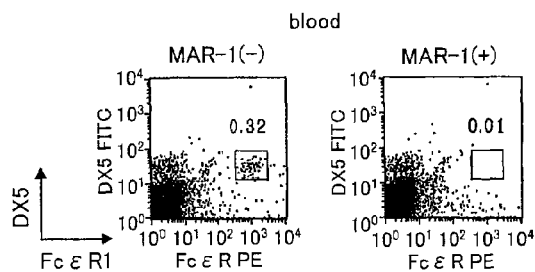
Figure 9:
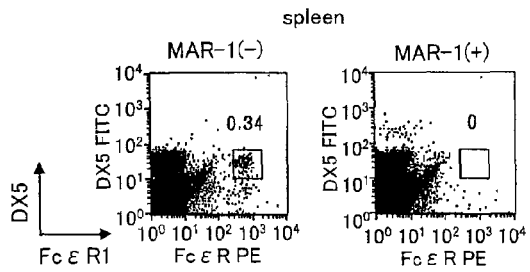
Figure 9:
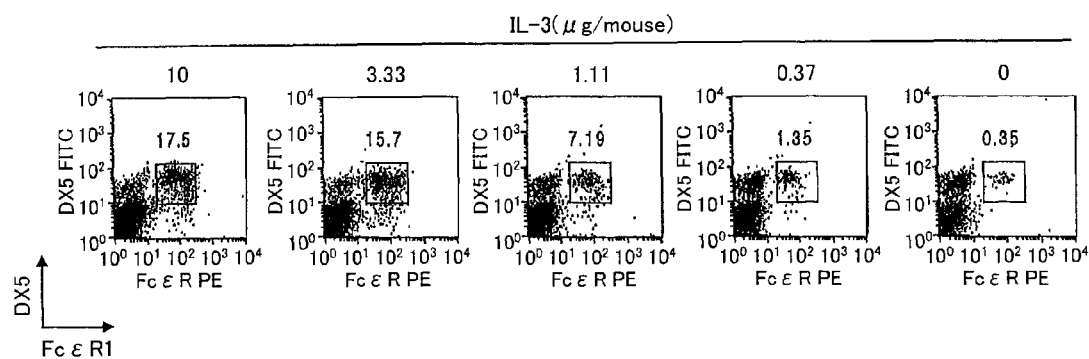

Finally, to reveal direct evidence that antigen presentation by endogenous basophils is critically important to the induction of early Th2 response in vivo, DNP-OVA/anti-DNP IgE complex was injected into naive mice or mice depleted of basophils. For depletion of basophils, an antibody to FcεR1α (MAR-1) was intraperitoneally injected twice daily for 3 days, by following the method by Denzel et al. Complete depletion of basophils in spleen and liver was achieved 2 days after the final injection of MAR-1 (not control hamster IgG) (FIG. 9). As a result of measuring expression of IL-4 in basophils by measuring expression of GFP as a reporter of IL-4 by FACS over time after the injection of DNP-OVA (100 μg)/anti-DNP IgE (200 μg), a remarkable production of IL-4 were observed in basophils 12 hours after or 24 hours after injection. Furthermore, 4 days after injection, splenic CD4$^+$ cells were prepared; these cells were stimulated with OVA-pulsed APCs, and IL-4, IL-13, and IFN-γ content in its culture supernatant were measured. As a result, it was found that a complex of DNP-OVA/anti-DNP IgE into naive mice, not basophils-depleted mice, promptly induced Th2 cells in the spleen (FIG. 4($c$)).

Accordingly, it was demonstrated that unique professional APCs preferentially induce Th2 cells in vitro and in vivo. Like conventional APCs, basophils express MHC class II, CD80 and CD86, internalize and process antigen protein and express peptide in association with MNHC class II (FIG. 2($a$), FIG. 3). In contrast, mast cells express these molecules extremely modestly (FIG. 2($a$)). Furthermore, basophils heavily pulsed with OVA peptide strongly induce naive CD4$^+$ T cells to develop into Th2 cells, while OVA-pulsed mast cells failed to induce the naive CD4$^+$ T cells to develop into the Th2 cells. This suggests their striking difference in induction of Th2 response in vivo (FIG. 4($a$)). As reported previously, the Th2 cells markedly increase the number of basophils in the spleen and lymph node, and there are apparent mutual positive feedback regulation between the levels of basophils and of Th2 cells.

Thus, down-regulation of basophils is an important strategy for the treatment of Th2-IgE response. IgE is also an important target molecule, because IgE initiates positive feedback regulation between basophils and Th2 cells. Basophils have been generally accepted as cells producing IL-4 and transferring antigen to DCs that do the actual antigen presentation. It is thought as important to recognize potent APC function of basophils themselves, in order to understand a mechanism of how patients exhibiting a positive reaction to a single allergen become more strongly positive to the same antigen or how those patients develop positive reactions to multiple allergens. It was suspected that multiple Th2 cell clones are induced by the basophils sensitized with polyclonal antibody uptaking corresponding allergens and having those basophils present multiple T cell epitopes. Human cord blood cells also become contaminated with basophils in a case of expanding the cord blood cells in a IL-3 containing medium, which these basophils cause expression of MHC class II molecules, suggesting their potential to induce Th2-IgE response in patients receiving cord blood cells which expanded in IL-3 containing medium.

As described above, the present invention demonstrates that basophils are antigen-presenting cells which induce Th2-dominant immune response. Moreover, the present invention also demonstrates a possibility of controlling allergic diseases by controlling basophils in various methods.

The inventors of the present invention demonstrated that basophils express MHC class II molecules and CD80/86, and produce IL-4 under various stimulatory conditions. This suggests a potential of basophils to induce naive CD4$^+$ T cells to develop into Th2 cells in the absence of professional antigen-presenting cells (APCs).

Ovalbumin (OVA)-specific naive CD4$^+$ cells cultured with basophils, OVA peptide, or DNP-OVA in the presence of IL-3 and absence of IL-4, develop into Th2 cells. This Th2-inducing action of basophils was completely abolished by IL-4-deficient basophils. This suggests that IL-4 released by OVA-pulsed basophils is critical for the development of Th2 cells. Furthermore, basophils cultured with DNP-OVA and anti-DNP-IgE internalize and process more OVA than basophils cultured with DNP-OVA alone. Hence, these basophils showed more potent APC activity than basophils cultured with DNP-OVA alone.

Furthermore, intravenous administration of heavily OVA-pulsed basophils cells strongly and rapidly induced Th2 cells, whereas that of OVA-pulsed mast cells did not induce Th2 cells. Following the induction by basophils of Th2 cells, the produced Th2 cells in turn helps OVA-stimulated B cells to produce OVA-specific IgE antibodies. This suggests that positive feedback of Th2-IgE response is regulated by internalization of IgE-dependent antigen by the basophils.

3. Drawings

FIG. 1($a$) through FIG. 1($d$) show antigen presentation by parasite-induced splenic basophils. FIG. 1($a$) shows a result of flow cytometry analyzing the expression of FcεR1 and c-kit by freshly prepared splenic non-B, non-T cells from BALB/c mice or BALB/c mice inoculated for 10 days with $S.$ $venezuelensis$ third-stage larvae. Splenic non-B, non-T cells from mice inoculated with or without $S.$ $venezuelensis$ were further categorized into FcεR1$^+$/c-kit$^-$ cells with a FACS Aria. Numbers represent the proportion of FcεR1$^+$/c-kit$^-$ cells.

FIG. 1($b$) shows a Bio-Plex analysis of cytokines content in a supernatant harvested upon culturing sorted basophils described in FIG. 1($a$) for 24 hours with IL-3 (20 U/mL) in 96-well plates at a density of $1\times10^5$ per 0.2 mL per well. Data are representative of two independent experiments (mean and s.e.m. of three mice).

FIG. 1($c$) shows a result of analyzing, by FACS, cytosolic IL-4 and IFN-γ, upon carrying out the following processes: naive DO11.10 CD4$^+$ CD62L$^+$ T cells ($1\times10^5$ per mL) were stimulated for 7 days in 48-well plates with IL-2 (100 pM), IL-3 (20 U/mL), and OVA$_{323-339}$ (1 μM) in the presence of irradiated T cell-depleted BALB/c spleen cells (ΔT-spleen) or irradiated splenic basophils from *S. venezuelensis*-infected mice (parasite-induced basophils) (without IL-4 (Th0 condition)) ($1 \times 10^5$ cells per mL each), and after initiation of priming, washed and then recultured for 4 hours with PMA (50 g/mL) plus ionomycin (500 ng/mL). Numbers indicate the proportion of IL-4$^+$ or IFN-γ$^+$ cells gated on CD4$^+$ T cells.

FIG. 1(*d*) shows an expression of the 3Rα chain on CD4$^+$ T cells which is cultured for 7 days with ΔT-spleen or parasite-induced basophils shown by flow cytometry in FIG. 1(*c*). Proportion of the IL-33Rα chain$^+$ cells in CD4$^+$ cells is indicated by percentage.

FIG. 2(*a*) through FIG. 2(*c*) show expression of MHC class II molecules on the basophils. FIG. 2(*a*) shows a result of staining with surface markers on bone marrow-derived and FACS-sorted basophils and mast cells (shown in FIG. 6) and T cell-depleted spleen cells (ΔT-spleen). Filled histograms indicate the markers, and the lines indicate the unstained cells.

FIG. 2(*b*) shows a result analyzed by flow cytometry of expression for MHC class II (I-A) and FcεR1, of bone marrow-derived and FACS-sorted basophils and mast cells. Proportions of FcεR1$^+$I-A$^+$ cells are indicated by percentage. Results are representative of four independent experiments.

FIG. 2(*c*) shows a result of analysis by flow cytometry, of expression for c-kit and CD203c (left) and HLA-DR among CD203c$^+$c-kit$^-$ cells (right), of CD34$^+$ cord blood cells cultured for 7 days with human IL-3 (10 ng/mL). Results are representative of three independent experiments.

FIG. 3(*a*) through FIG. 3(*d*) show results of antigen presentation by bone marrow-derived basophils. Naive splenic CD4$^+$ CD62L$^+$ T cells ($1 \times 10^5$ cells per mL) from DO11.10 mice were stimulated with IL-2 (100 pM), IL-3 (20 U/mL) and OVA$_{323-339}$ (1 μM) (FIG. 3(*a*) and FIG. 3(*b*)), DNP-OVA (100 μg/mL) (FIG. 3(*c*)), and DNP-OVA (6.25 to 100 μg/mL) with or without anti-DNP IgE mAb (10 μg/mL) (FIG. 3(*d*)), in the presence of irradiated T cell-depleted BALB/c splenocytes (ΔT-spleen) ($5 \times 10^5$ cells per mL), irradiated bone marrow-derived purified basophils (WT; wild-type mice or G4/G4; IL-4-deficient mice), mast cells or splenic DCs in 48-well plates in a total 1-mL volume of medium for 7 days (Th0 condition). For induction to develop into Th2 cells, IL-4 (1000 U/mL) was further added to the culture (Th2 condition). After initial priming, cells were washed and recultured with PMA (50 ng/mL) plus ionomycin (500 ng/mL) for 4 hours and analyzed by FACS for expression of cytosolic IL-4 and IFN-γ. Numbers represent the percentage of IL-4$^+$ or IFN-γ$^+$ cells gated on CD4$^+$ T cells. Results are representative of three independent experiments.

Figure 4:
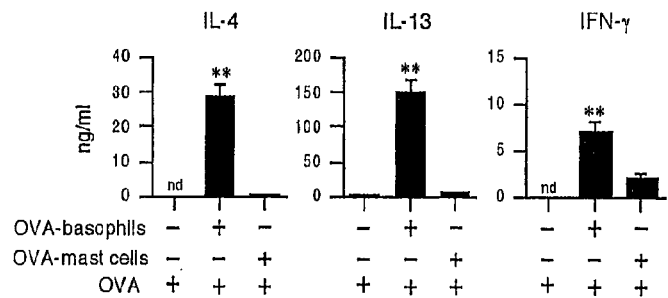
FIG. 4(a) is a view showing a result measured by ELISA, of an amount of IL-4, IL-13 and IFN-γ in a culture supernatant obtained by: culturing basophils or mast cells with DNP-OVA/anti-DNP IgE; transferring the cultured basophils or mast cells into normal mice; 4 days after adoptive transfer, intravenously challenging the mice with intact OVA protein; and 2 days after the challenge injection, stimulating splenic CD4$^+$ cells from each mouse with APC (ΔT-spleen) pulsed with OVA.
FIG. 4(b) is a view showing a result measured by ELISA, of OVA-specific IgE antibodies and IgG1 antibodies in serums collected by: culturing basophils with DNP-OVA/anti-DNP IgE; transferring the cultured basophils into normal mice; 1 week after adoptive transfer, intravenously challenging the mice with intact OVA protein; and collecting the serums on the day of the challenge injection.
FIG. 4(c) is a view showing a result measured by ELISA, of amounts of IL-4, IL-13, and IFN-γ in a culture supernatant obtained as follows: culturing basophils with DNP-OVA/anti-DNP IgE; transferring the cultured basophils into normal mice; 1 week after adoptive transfer, intravenously challenging the mice with intact OVA protein; and 2 weeks after the challenge injection, stimulating for 5 days splenic CD4$^+$ cells from each mouse with APC (ΔT-spleen) pulsed with OVA.
FIG. 4(d) is a view showing a result of measuring a proportion of CD4$^+$CD62L$^{low}$IL33Rα$^+$ Th2 cells in a spleen prepared as follows: culturing basophils with DNP-OVA/anti-DNP IgE; transferring the cultured basophils into normal mice; 1 week after adoptive transfer, intravenously challenging the mice with intact OVA protein; and preparing the spleen from the mice 2 weeks after the challenge injection.
FIG. 4(e) is a view showing an observation result of IL-4 production in peripheral blood, spleen, and bone marrow of mice before and after the mice are injected with DNP-OVA/anti-DNP IgE by a dose as indicated, the result which is observed by expression of GFP as a reporter of IL-4.
FIG. 4(f) is a view showing a result measured by ELISA of amounts of IL-4, IL-13, and IFN-γ in a culture supernatant obtained by the following method: intraperitoneally administering mice with anti-FcεR1α (MAR-1) before and after the mice are injected with DNP-OVA/anti-DNP IgE of a dose as indicated; 4 days after the injection of DNP-OVA/anti-DNP IgE, preparing splenic CD4$^+$ cells from the mice; and stimulating these splenic CD4$^+$ cells with APC (ΔT-spleen) pulsed with OVA for 5 days.
FIG. 4(g) is a view showing a result measured by ELISA of amounts of IL-4, IL-13, and IFN-γ in a culture supernatant obtained by the following method: intraperitoneally administering mice with anti-FcεR1α (MAR-1) before and after the mice are injected with DNP-OVA/anti-DNP IgE of a dose as indicated; 4 days after the injection of DNP-OVA/anti-DNP IgE, preparing the splenic CD4$^+$ cells from the mice; and stimulating these splenic CD4$^+$ cells with APC (ΔT-spleen) pulsed with OVA for 5 days.
FIG. 4(h) is a view showing a result measured by ELISA of OVA-specific IgE and IgG1 antibodies in serums collected from mice which were: injected with DNP-OVA/anti-DNP IgE of a dose as indicated; and 4 days after the injection of the DNP-OVA/anti-DNP IgE, intravenously challenged with intact OVA protein. The serums were collected on the day of the challenge injection. In order to deplete or increase the number of basophils, anti-FcεR1α (MAR-1) is injected into the mice.
FIG. 4(i) is a view showing a result measured by ELISA of OVA-specific IgE and IgG1 antibodies in serums collected from mice which were: injected with DNP-OVA/anti-DNP IgE of a dose as indicated; and 4 days after the injection of the DNP-OVA/anti-DNP IgE, intravenously challenged with intact OVA protein. The serums were collected on the day of the challenge injection. In order to deplete or increase the number of basophils, IL-3 is injected into the mice.
Figure 4:
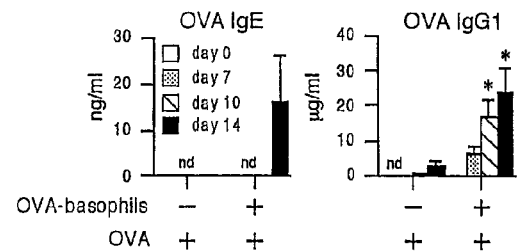
Figure 4:
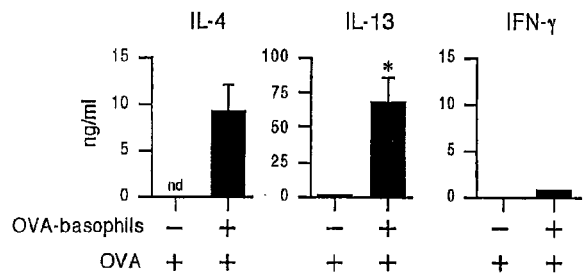
Figure 4:
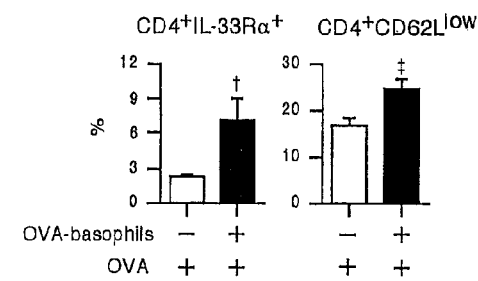
Figure 4:
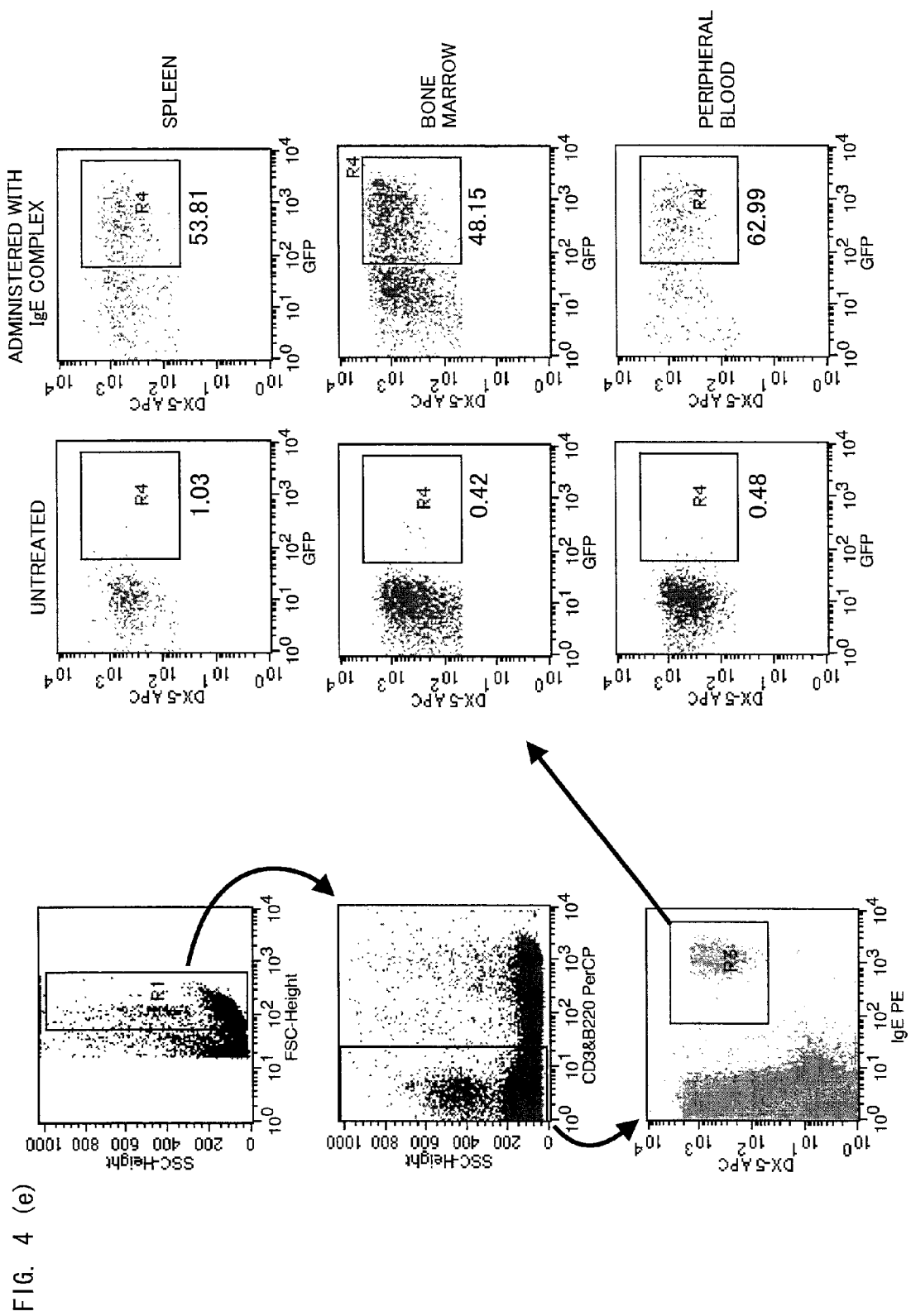
Figure 4:
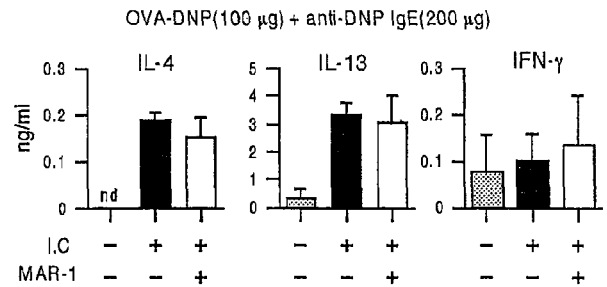
Figure 4:
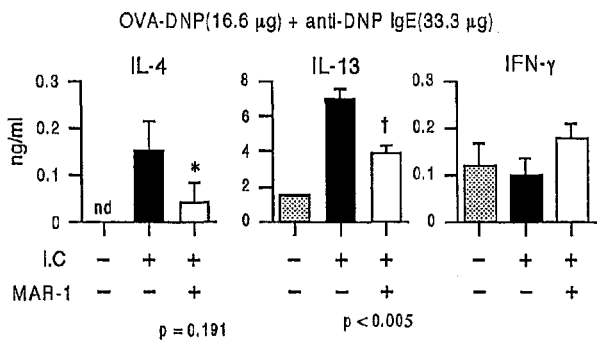
Figure 4:
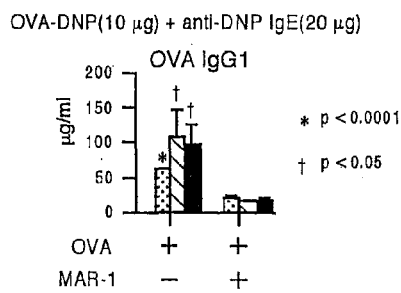
Figure 4:
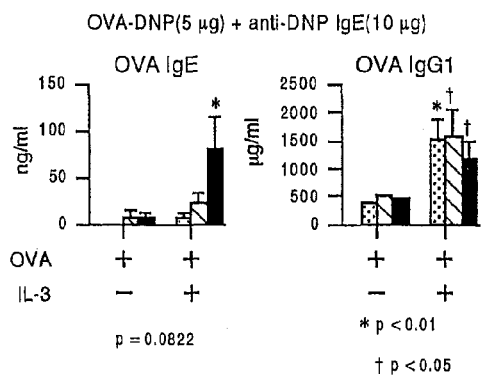

FIG. 4(*a*) through FIG. 4(*i*) illustrate basophils-induced antigen-specific Th2 response in vivo. In FIG. 4(*a*) through FIG. 4(*d*), bone marrow-derived and FACS sorted basophils or mast cells ($5 \times 10^5$ cells per mL each) were cultured with IL-3 (20 U/mL), DNP-OVA (100 μg/mL), and anti-DNP IgE mAb (10 μg/mL) in 48-well plates for 16 hours. After priming, basophils or mast cells (each $2.5 \times 10^5$ cells per mouse) were transferred into BALB/c mice (5 mice per group) through the tail vein. Four days (FIG. 4(*a*)) or 1 week (FIG. 4(*b*) through FIG. 4(*d*)) after adoptive transfer, the mice were intravenously challenged with OVA protein (100 μg per mouse). Control mice were injected with OVA protein (100 μg) alone. After the challenging injection (day 0), serums were collected and OVA-specific IgE antibodies and IgG1 antibodies were determined by ELISA (FIG. 4(*b*)). Two days (FIG. 4(*a*)) or 2 weeks (FIG. 4(*c*)) after challenge injection, splenic CD4$^+$ cells ($2 \times 10^5$ cells per 0.2 mL per well) from each mouse were restimulated with OVA protein (100 μg/mL) in the presence of irradiated ΔT-spleen ($2 \times 10^5$ cells per 0.2 mL per well) in 96-well plates.

In FIG. 4(*e*) through FIG. 4(*g*), BALB/c mice (5 mice per group) were injected with a mixture of OVA-DNP and anti-DNP IgE antibody (immune complex: I.C) as indicated doses. For depletion of basophils, the mice were injected with 5 μg anti-FcεR1α (MAR-1) intraperitoneally twice daily for a continuous 3 days before and after I.C injection. Four days after I.C injection, splenic CD4$^+$ cells ($2 \times 10^5$ cells per 0.2 mL per well) from each mouse were restimulated with OVA protein (100 μg/mL) in the presence of irradiated ΔT-spleen ($2 \times 10^5$ cells per 0.2 mL per well). Five days after in vitro stimulation, supernatants thereof were harvested and tested for IL-4, IL-13 and IFN-γ production, by ELISA (FIG. 4(*a*), FIG. 4(*c*), FIG. 4(*f*), FIG. 4(*g*)). Results are representative of two independent experiments (mean and s.e.m. of five mice).

In FIG. 4(*a*), ** denotes P<0.0001 by Student's t-test as compared to mice transferred with mast cells and injected with OVA. In FIG. 4(*b*) through FIG. 4(*d*), * denotes P<0.01, † denotes P<0.05, and ‡ denotes P<0.005 (each of which as compared to control groups injected with OVA alone). In FIG. 4(*b*), * denotes P=0.191 and † denotes P<0.005 as a result by Student's t-test as compared to groups depleted of basophils.

In FIGS. 4(*h*) through FIG. 4(*i*), BALB/c mice (5 mice per group) were injected with a mixture (I.C) of OVA-DNP and anti-DNP IgE antibody as indicated doses. Four days after 1.0 injection, mice were intravenously challenged with OVA protein (100 μg per mouse) and serums were collected and OVA-specific IgE and IgG1 antibodies were determined by ELISA. For depletion or increase in the number of basophils, the mice were injected with anti-FcεR1α (MAR-1) or IL-3. Note that * denotes P<0.001 and † denotes P<0.05 as a result by Student's t-test as compared to control groups.

Figure 5:
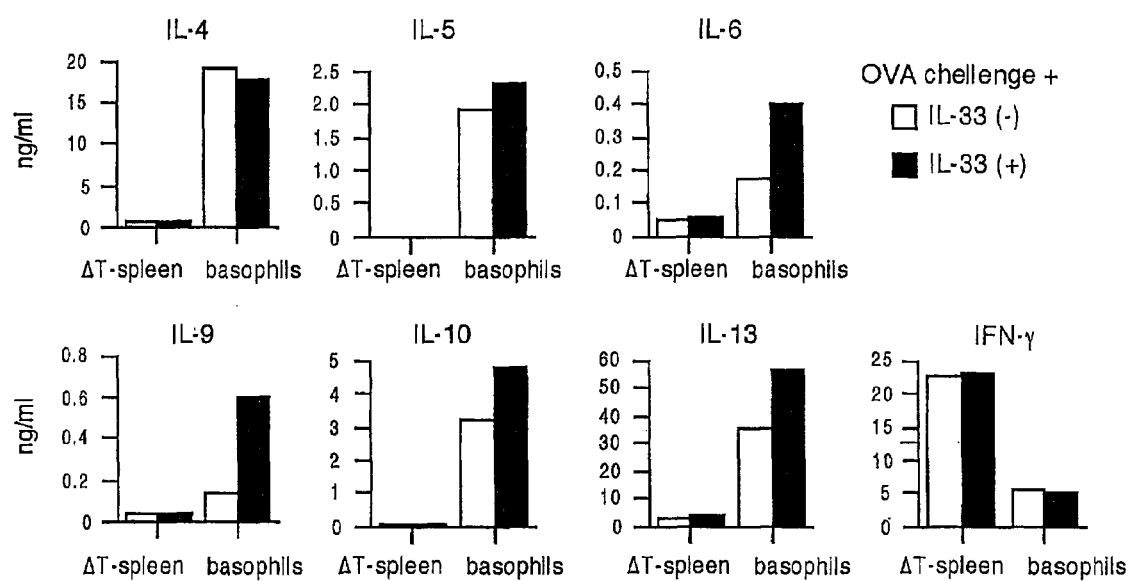
FIG. 5 is a view showing cytokines production from basophils-driven Th2 cells. Naive T cells were stimulated with OVA$_{323-339}$ for 7 days in the presence of T cell-depleted mice splenocytes (ΔT-spleen) or basophils from parasite-infected mice, to produce CD4$^+$ T cells. The produced CD4$^+$ T cells were challenged with OVA$_{323-339}$ with or without IL-33 for 48 hours, in the presence of irradiated T cell-depleted mice splenocytes, to collect supernatants thereof.

FIG. 5 shows cytokines production from basophils-driven Th2 cells. Naive CD4$^+$ CD62L$^+$ T cells ($1 \times 10^5$ cells per mL) from DO11.10 were stimulated with IL-2 (100 pM), IL-3 (20 U/mL), and OVA$_{323-339}$ (1 μM), in the presence of irradiated T cell-depleted BALB/c splenocytes (ΔT-spleen), or irradiated splenic basophils from *S. venezuelensis*-infected mice (parasite-induced basophils) (without IL-4 (Th0 condition)) ($5 \times 10^5$ cells per mL each) in 48-well plates for 7 days. After initial priming, CD4$^+$ T cells ($1 \times 10^5$ cells per 0.2 mL per well) were restimulated with IL-2 (100 pM) and OVA$_{323-339}$ (1 μM) in the presence of irradiated T cell-depleted BALB/c splenocytes ($1 \times 10^5$ cells) in 96-well plates, with or without IL-33 (100 ng/mL) for 48 hours. Supernatants were harvested and tested for cytokine production by the Bio-Plex system. Results are representative of three independent experiments.

FIG. 6(*a*) through FIG. 6(*d*) show results of purification and histological examination of mouse bone marrow-derived basophils and human peripheral blood basophils. In FIG. 6(*a*), bone marrow cells from BALB/c mice were cultured with IL-3 (10 U/mL) for 10 days and were analyzed for expression of FcεR1 and c-kit by flow cytometry, and then sorted into FcεR1$^+$/c-kit$^-$ (basophils) cell populations and FcεR1$^+$/c-kit$^+$ (mast cells) cell populations, by FACS Aria. Percentages of cells in selected populations are as indicated.

FIG. 6(*b*) shows an observation result of the sorted FcεR1$^+$/c-kit$^-$ (basophils) and FcεR1$^+$/c-kit$^+$ (mast cells) cell population through an electron microscope. Scale bar: 1 μm.

FIG. 6(*c*) shows a measurement result of expression for HLA-DR and CD203c of negative enriched human peripheral blood mononuclear cells (CD3$^-$, CD7$^-$, CD14$^-$, CD15$^-$, CD16$^-$, CD19$^-$, CD36$^-$, CD45RA$^-$, and CD235a$^-$) immediately after selection (left) or after culturing for 24 hours in the presence of human IL-3 (10 ng/mL) (right).

FIG. 6(d) shows a result of sorted CD203c⁺/HLA-DR⁺ cell populations being subjected to Wright-Giemsa staining (left; 100×), and being subjected to electron microscopic examination (right). Scale bar: 1 μm.

FIG. 7 shows basophils-induced antigen-specific T cell proliferation. Naive splenic CD4⁺ CD62L⁺ T cells (5×10⁴ cells per mL) from DO11.10 mice were stimulated with IL-2 (100 pM), IL-3 (20 U/mL) and $OVA_{323-339}$ (1 μM) or DNP-OVA (6.25 to 100 μg/mL) with or without anti-DNP IgE mAb (10 μg/mL), in the presence of irradiated ΔT-spleen or purified basophils (2.5×10⁵ cells per mL) in 96-well plates for 4 days. DNA synthesis was measured by adding 1 μCi of [³H] during the final 16 hours.

FIG. 8(a) through FIG. 8(d) show Th2 cytokines production from bone marrow-derived basophils and mast cells. FIG. 8(a) shows a result obtained by stimulating naive splenic CD4⁺ CD62L⁺ T cells (1×10⁵ cells per mL) from DO11.10 mice with $OVA_{323-339}$ (1 μM) or DNP-OVA (100 μg/mL) with or without anti-DNP IgE mAb (10 μg/mL), in the presence of irradiated ΔT-spleen or purified basophils (5×10⁵ cells per mL) in 48-well plates for 24 hours.

FIG. 8(b) shows a result representative of five independent experiments (means and s.e.m.), of an assessment of IL-4 or IL-13 production by ELISA, in which bone marrow-derived and FACS sorted basophils or mast cells (1×10⁵ cells per 0.2 mL per well each) were restimulated with IL-3 (20 U/mL) or DNP-OVA (100 μg/mL) with or without anti-DNP IgE mAb (10 μg/mL) in 96-well plates for 16 hours, and supernatants were harvested for the testing. Note that "nd" denotes "not detected".

FIG. 8(c) shows a result of analysis by RT-PCR for TLR genes and β-actin expression, of mRNAs extracted from bone marrow-derived and FACS sorted basophils or mast cells. As positive controls (posi.) for TLRs mRNA, mRNAs extracted from murine splenic cells were used.

FIG. 8(d) shows a representative of five independent experiments (means and s.e.m.), of an assessment of IL-4, IL-6, or IL-13 production by ELISA, in which bone marrow-derived and FACS sorted basophils or mast cells (1×10⁵ cells per 0.2 mL per well) were restimulated with IL-3 (20 U/mL) plus IL-18 (50 ng/mL), IL-33 (100 ng/mL), LPS (1 μg/mL), or PGN (10 μg/mL), in 96-well plates for 24 hours, and supernatants were harvested for the testing.

FIG. 9(a) through FIG. 9(e) show depletion of basophils having anti-FcεR1α. FIG. 9(a) through FIG. 9(d) show flow cytometry and frequency of basophils (FcεR1⁺/c-kit⁻ cells or FcεR1⁺/DX5⁺ cells) in BALB/c injected intraperitoneally twice daily for 3 days with 5 μg anti-mouse Fcε1α (MAR-1 (+)) or PBS (MAR-1(−)). Two days after the last injection, the number of basophils were quantified (FIG. 9(a): spleen, FIG. 9(b): liver). Subsequently, mice were injected with a mixture of DNP-OVA plus anti-DNP IgE, twice daily for an additional 3 days with MAR-1 or PBS. After intravenously challenging with OVA, at 4 days after I.C injection, the mice were additionally treated with MAR-1 or PBS for a continuous 5 days per week for 2 weeks. One week or two weeks after the OVA challenge, the number of basophils were quantified in the blood (FIG. 9(c)) or spleen (FIG. 9(d)), respectively.

FIG. 9(e) shows representative data from five independent mice, of frequency of basophils (FcεR1⁺/DX5+ cells) from BALB/c mice injected with IL-3 (0 to 10 μg/body weight/2 weeks) using an osmotic pump. The percentage shown represents the proportion of FcεR1⁺/c-kit⁻ cells or FcεR1⁺/DX5⁺ cells gated on splenic non-B, non-T cells.

Figure 10:
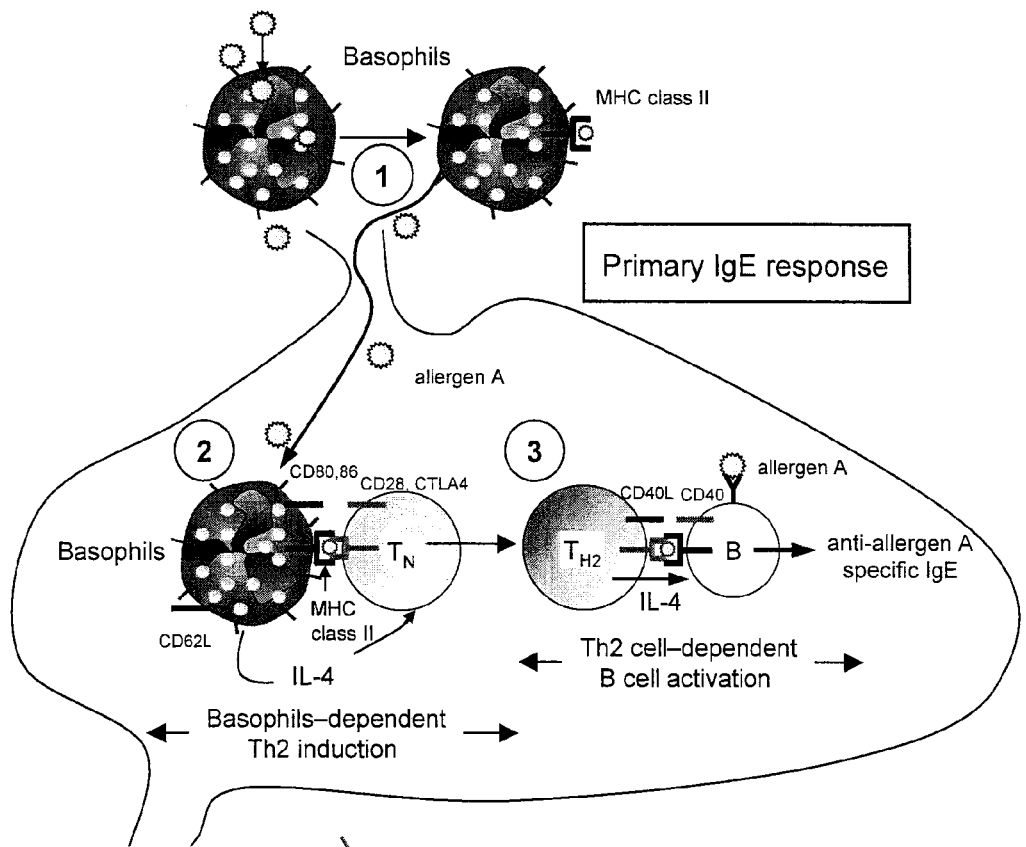
FIG. 10 is a schematic view illustrating a mechanism of Th2/IgE induction in vivo by antigen-pulsed basophils or IgE complex.
Figure 10:
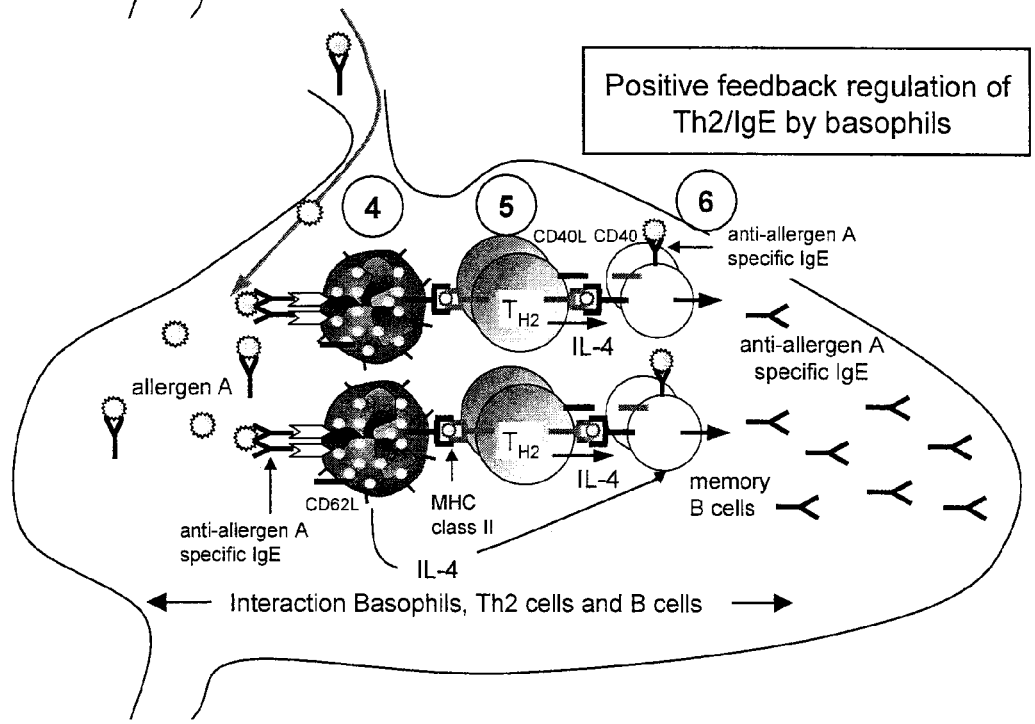

FIG. 10 is a schematic view illustrating a Th2-IgE induction in vivo by antigen-pulsed basophils. When antigen A (e.g., OVA) is administered to a normal animal, first, the antigen A is taken into basophils (1 in FIG. 10). OVA-pulsed basophils circulate to peripheral lymphoid organ (e.g., spleen), which provides IL-4 stimulation and antigen peptide/MHC class II stimulation to OVA-specific naive CD4⁺ T cells. Subsequently, OVA-specific naive CD4⁺ T cells develop into Th2 cells caused by just the antigen stimulation and IL-4 stimulation from the basophils, and without help from DCs (i.e., basophils-dependent Th2 cells induction phase; 2 in FIG. 10). Simultaneously, OVA administered into a living body also circulate in the peripheral lymphoid organ. Here, OVA bind with an antigen receptor of OVA-specific B cells. B cells pulsed with OVA stimulates OVA-specific Th2 cells, thereby causing the stimulated Th2 cells to produce CD40 ligand and IL-4. The produced CD40 ligand and IL-4 stimulate the OVA-pulsed B cells and induce OVA-specific IgE production (i.e., Th2 cell-dependent B cell activation phase; 3 in FIG. 10). Once the OVA-specific IgE is produced, IgE immune complex including OVA and anti-OVA-specific IgE antibodies binds with FcεR1 on basophils (i.e., basophils are sensitized with IgE; 4 in FIG. 10). Caused by the stimulation of the sensitized basophils, memory Th2 cells are stimulated and proliferated (5 in FIG. 10). Furthermore, OVA-stimulated memory B cells, following activation by the memory Th2 cells, produce IgE antibodies having very high affinity bonding to OVA (6 in FIG. 10).

INDUSTRIAL APPLICABILITY

The present invention reveals a mechanism of Th2-type immune response which was unknown until now, particularly of early IL-4 production. Hence, the present invention is suitably usable for development of new remedies and therapeutic methods for Th2-type diseases. Namely, the present invention is usable in a wide variety of fields, including the medical field and the pharmaceutical field.

The invention claimed is:

1. A screening method of screening a therapeutic agent of a Th2-type disease, comprising the steps of:
    (a) producing a complex of antigen and IgE binding to the antigen, the complex being bound to no cell or base material;
    (b) culturing basophils in the presence of the complex;
    (c) administering to a mouse the basophils cultured in the step (b), to prepare a model mouse;
    (d) administering a candidate substance to the model mouse; and
    (e) measuring whether or not improvement is attained of the Th2-type disease, in the model mouse to which the candidate substance is administered.

2. The screening method according to claim 1, wherein the disease is selected from the group consisting of: hay fever, bronchial asthma, atopic dermatitis, allergic enteritis, allergic conjunctivitis, and allergic rhinitis.

3. A preparation method of preparing a model mouse of a Th2-type disease, the method comprising the steps of:
    producing a complex of an antigen and IgE binding to the antigen, the complex being bound to no cell or base material;
    culturing basophils in the presence of the complex; and
    administering to a mouse the basophils having been cultured in the presence of the complex.

4. The preparation method according to claim 3, wherein the disease is bronchial asthma, and the preparation method further comprises the step of administering the basophils having been cultured in the presence of the complex, by transnasal administration.

* * * * *